United States Patent
Van Egmond et al.

(10) Patent No.: US 7,196,239 B2
(45) Date of Patent: Mar. 27, 2007

(54) METHANOL AND ETHANOL PRODUCTION FOR AN OXYGENATE TO OLEFIN REACTION SYSTEM

(75) Inventors: Cornelis F. Van Egmond, Pasadena, TX (US); Andrew Argo, League City, TX (US); Teng Xu, Houston, TX (US); Marcel Johannes Janssen, Kessel-Lo (BE); Jaimes Sher, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 363 days.

(21) Appl. No.: 10/716,894

(22) Filed: Nov. 19, 2003

(65) Prior Publication Data

US 2005/0107482 A1 May 19, 2005

(51) Int. Cl.
*C07C 1/00* (2006.01)
*C07C 27/00* (2006.01)

(52) U.S. Cl. ...... 585/640; 585/639; 518/700; 518/703; 518/707; 518/713; 518/714

(58) Field of Classification Search ........ 585/638–640; 518/700, 703, 707, 713, 714
See application file for complete search history.

(56) References Cited

U.S. PATENT DOCUMENTS

| | | | |
|---|---|---|---|
| 4,014,913 A | 3/1977 | Ellgen et al. | 260/449 |
| 4,111,837 A | 9/1978 | Taylor | 252/430 |
| 4,122,110 A | 10/1978 | Sugier et al. | 260/449.5 |
| 4,133,966 A | 1/1979 | Pretzer et al. | 568/902 |
| 4,233,466 A | 11/1980 | Fiato | 568/902 |
| 4,239,924 A | 12/1980 | Pretzer et al. | 568/902 |
| 4,239,925 A | 12/1980 | Pretzer et al. | 568/902 |
| 4,253,987 A | 3/1981 | Fiato | 252/429 R |
| 4,270,015 A | 5/1981 | Knifton | 585/324 |
| 4,304,946 A | 12/1981 | Isogai et al. | 568/902 |
| 4,324,927 A | 4/1982 | Gauthier-Lafaye et al. | 568/902 |
| 4,328,379 A | 5/1982 | Devon | 568/902 |
| 4,339,545 A | 7/1982 | Knifton | 518/700 |
| 4,371,724 A | 2/1983 | Lin et al. | 568/902 |
| 4,398,050 A | 8/1983 | Hofstadt et al. | 585/640 |
| 4,424,383 A | 1/1984 | Cornils et al. | 568/902 |

(Continued)

FOREIGN PATENT DOCUMENTS

DE  31 13 838  7/1982

(Continued)

OTHER PUBLICATIONS

J P Leonard et al: "Non-Conventional Sources for Ethylene?" Energy Progress, vol. 1, No. 1-4, 1981, pp. 41-44 US New York, NY.

(Continued)

*Primary Examiner*—Glenn Caidarola
*Assistant Examiner*—In Suk Bullock

(57) ABSTRACT

The present invention provides various processes for producing light olefins from methanol and ethanol, optionally in a mixed alcohol stream. In one embodiment, the invention includes directing a first syngas stream to a methanol synthesis zone to form methanol and directing a second syngas stream and methanol to a homologation zone to form ethanol. The methanol and ethanol are directed to an oxygenate to olefin reaction system for conversion thereof to ethylene and propylene.

34 Claims, 4 Drawing Sheets

U.S. PATENT DOCUMENTS

| | | | | |
|---|---|---|---|---|
| 4,424,384 | A | 1/1984 | Lin et al. | 568/902 |
| 4,596,782 | A | 6/1986 | Courty et al. | 502/302 |
| 4,605,677 | A | 8/1986 | Knifton | 518/700 |
| 4,622,343 | A | 11/1986 | Knifton et al. | 518/700 |
| 4,638,106 | A | 1/1987 | Pieters et al. | 585/640 |
| 4,670,473 | A * | 6/1987 | Walker et al. | 518/706 |
| 4,670,620 | A | 6/1987 | Jacobs et al. | 585/640 |
| 4,698,452 | A | 10/1987 | Le Van Mao et al. | 585/640 |
| 4,751,248 | A | 6/1988 | Lin et al. | 518/707 |
| 4,752,623 | A | 6/1988 | Stevens et al. | 518/714 |
| 4,791,141 | A | 12/1988 | Chaumette et al. | 518/713 |
| 4,825,013 | A | 4/1989 | Quarderer et al. | 568/902.2 |
| 4,849,575 | A * | 7/1989 | Lewis | 585/640 |
| 4,954,665 | A | 9/1990 | Vidal | 568/902.2 |
| 5,070,016 | A | 12/1991 | Hallberg | 435/132 |
| 5,169,869 | A | 12/1992 | Miller et al. | 518/713 |
| 5,493,064 | A | 2/1996 | Vanderspurt et al. | 568/905 |
| 5,627,295 | A | 5/1997 | Sofianos et al. | 556/27 |
| 5,756,421 | A | 5/1998 | Choudhary et al. | 502/328 |
| 6,114,279 | A * | 9/2000 | Fukui et al. | 502/342 |
| 6,437,208 | B1 * | 8/2002 | Kuechler et al. | 585/640 |
| 6,441,262 | B1 | 8/2002 | Fung et al. | 585/640 |
| 2001/0047040 | A1 | 11/2001 | Agee et al. | 518/704 |
| 2002/0147376 | A1 | 10/2002 | Fung et al. | 585/638 |

FOREIGN PATENT DOCUMENTS

| | | |
|---|---|---|
| DE | 257740 | 6/1988 |
| EP | 0109645 | 11/1983 |
| GB | 2 078 745 | 1/1982 |
| GB | 2 083 465 | 3/1982 |
| WO | WO 2004/060841 | 7/2004 |

OTHER PUBLICATIONS

Database Chemabs 'Online! Chemical Abstracts Service, Columbus, Ohio, US; Takeuchi, Kazuhiko: "Synthetic process of basic chemical from syngas", retrieved from STN Database accession No. 1997: 2165 *abstract* & Shokubai, 38(8), 604-610 Coden: Shkuaj; ISSN: 0559-8958, 1996.

Japanese Journal article Kazuhiko Takeuchi, "Synthetic Process of Basic Chemicals from Syngas," 38(8) Shokubai Gakkai pp. 604-610 (1996). (JP Article and Abstract).

Abstract for EP 0109645, Nov. 15, 1983, entitled "Simultaneous Production of Methanol and Ethanol".

U.S. Appl. No. 10/716,685, filed Nov. 19, 2003, "Methanol And Fuel Alcohol Production For An Oxygenate To Olefin Reaction System", Inventors: Marcel Janssen, Cor F. van Egmond, Luc Martens, and Jaimes Sher.

U.S. Appl. No. 10/717,006, filed Nov. 19, 2003, "Controlling The Ratio Of Ethylene To Propylene Produced In A Methanol/Ethanol Conversion Process", Inventors: Jaimes Sher, Cor F. van Egmond, Luc R.M. Martens, Marcel Janssen, James Lattner and Teng Xu.

Scheeline, et al, "Ethylene By Methanol Homologation", Process Economics Program, SRI International, Menlo Park, California, PEP Review No. 80-1-3, (Mar. 1981), pp. 1-20.

"Alternative Fuels and Chemicals From Synthesis Gas", Technical Progress Report No. 37, For the Period Jan. 1-Mar. 31, 1999, Air Products and Chemicals, Inc., Prepared for the United States Department of Energy, pp. 1-26.

Norcio, et al, "Higher Alcohol Synthesis From Methanol or Syngas", Department of Chemical Engineering, pp. 37-41.

Yamamoto and Inui, "Highly Effective Synthesis of Ethanol of $CO_2$ on Fe, Cu-Based Novel Catalysts", *Advances in Chemical Conversions for Mitigating Carbon Dioxide*, Studies in Surface Science and Catalysis, vol. 114, 1998 Elsevier Science B.V., pp. 513-516.

* cited by examiner

METHANOL AND ETHANOL PRODUCTION FOR AN OXYGENATE TO OLEFIN REACTION SYSTEM

FIELD OF THE INVENTION

The present invention relates to processes for forming light olefins. More particularly, the present invention relates to processes for forming light olefins from a mixed alcohol feedstock.

BACKGROUND OF THE INVENTION

Light olefins, defined herein as ethylene and propylene, are important commodity petrochemicals useful in a variety of processes for making plastics and other chemical compounds. Ethylene is used to make various polyethylene plastics, and in making other chemicals vinyl chloride, ethylene oxide, ethyl benzene and alcohol. Propylene is used to make various polypropylene plastics, and in making other chemicals such as acrylonitrile and propylene oxide.

The petrochemical industry has known for some time that oxygenates, especially alcohols, are convertible into light olefins. The preferred conversion process is generally referred to as an oxygenate to olefin (OTO) reaction process. Specifically, in an OTO reaction process, an oxygenate contacts a molecular sieve catalyst composition under conditions effective to convert at least a portion of the oxygenate to light olefins. When methanol is the oxygenate, the process is generally referred to as a methanol to olefin (MTO) reaction process. Methanol is a particularly preferred oxygenate for the synthesis of ethylene and/or propylene.

Depending on the respective commercial markets for ethylene and propylene, it may be desirable to vary the weight ratio of ethylene to propylene formed in an OTO reaction system. It has recently been discovered, however, that although percent conversion may vary with a change in reaction conditions, e.g., temperature or pressure, the selectivity of a methanol-containing feedstock for ethylene and propylene in an OTO reaction system generally remains constant with changes in reaction conditions. Thus, the need exists in the art for a process for varying the ratio of ethylene to propylene formed in an OTO reaction system.

SUMMARY OF THE INVENTION

This invention provides processes for forming ethylene and propylene from an alcohol-containing feedstock comprising methanol and ethanol. The methanol in the alcohol-containing feedstock is formed in a process for converting syngas to methanol in the presence of a catalyst composition, while the ethanol in the alcohol-containing feedstock is formed from a homologation reaction of methanol with carbon monoxide and optionally hydrogen. The alcohol-containing feedstock is directed to an oxygenate to olefin (OTO) reaction system for the conversion thereof to ethylene and propylene. The resulting weight ratio of ethylene to propylene formed in the OTO reaction system advantageously can be varied by varying the weight ratio of the methanol to ethanol in the alcohol-containing feedstock that is directed to OTO reaction system or by modifying reaction conditions, e.g., temperature.

In one embodiment, the present invention is directed to a process for producing light olefins. The process includes a step of contacting syngas in the presence of one or more metal containing catalysts to produce a first feedstock comprising methanol. A portion of the methanol is converted in a homologation zone to a second feedstock comprising ethanol. The first feedstock and the second feedstock are introduced to a process for converting the methanol and the ethanol in the presence of a molecular sieve catalyst composition to the light olefins. Optionally, the second feedstock further comprises methanol. Preferably, the first feedstock and the second feedstock are combined to form a combined feedstock prior to the introduction of the first feedstock and the second feedstock to the process for converting the methanol and the ethanol to the light olefins. In this embodiment, the combined feedstock comprises methanol, ethanol and optionally water, the weight majority of which preferably is removed from the combined feedstock prior to the step that the first and second feedstocks are introduced to the process for converting the methanol and the ethanol to the light olefins. The combined feedstock optionally further comprises light ends which comprise carbon monoxide, methane and hydrogen. In this embodiment, the light ends preferably are removed from at least a portion of the combined feedstock. The combined feedstock optionally has a methanol to ethanol weight ratio of from about 4.0:1.0 to about 99.0:1.0, or more preferably from about 9.0:1.0 to about 19.0:1.0. Preferably, the step of converting a portion of the methanol to a second feedstock comprises contacting the portion of the methanol with a homologation catalyst selected from the group consisting of: potassium oxides, cobalt-molybdenum sulfides, nickel-molybdenum sulfides and potassium carbonates. The converting step also preferably comprises contacting the portion of the methanol with the homologation catalyst in the presence of carbon monoxide, optionally hydrogen and optionally carbon dioxide. Carbon monoxide preferably is produced in the conversion of the methanol and the ethanol to the light olefins. The produced carbon monoxide optionally is separated from the light olefins and is directed to the homologation zone to provide a carbon monoxide source for the step of converting the methanol to the second feedstock. Optionally, the one or more metal-containing catalysts comprises one or more of carbon oxides, zinc oxides and aluminum oxides. Additionally, the process optionally comprises the step of contacting a natural gas stream with oxygen under conditions effective to convert the natural gas stream into the syngas.

In another embodiment, the invention is directed to an integrated process for producing light olefins. This inventive process includes a step of contacting syngas with one or more metal-containing catalysts to produce a first feedstock comprising methanol. A portion of the methanol preferably contacts carbon monoxide in the presence of a catalyst system to produce a second feedstock comprising ethanol. The first feedstock and the second feedstock, optionally in a combined stream, are introduced to a process for converting the methanol and the ethanol in the presence of a molecular sieve catalyst composition to the light olefins.

In another embodiment, the invention is directed to a process for producing light olefins, which includes a step of contacting a syngas stream with a methanol synthesis catalyst under first conditions effective to form a methanol-containing stream comprising methanol. At least a portion of the methanol-containing stream contacts carbon monoxide and a homologation catalyst under second conditions effective to form a mixed alcohol stream comprising methanol and ethanol. At least a portion of the mixed alcohol stream contacts a molecular sieve catalyst composition under third conditions effective to convert the methanol and the ethanol to the light olefins. Optionally, the mixed alcohol stream further comprises water and the process further comprises the step of separating a weight majority of the water from the mixed alcohol stream. The second conditions optionally comprise a holomogation reaction temperature of from about 204° C. to about 316° C. Optionally, the process further comprises a step of separating the mixed alcohol stream into a first fraction and a second fraction. The first fraction comprises a weight majority of the methanol present in the mixed alcohol stream, and the second fraction comprises a weight majority of the ethanol present in the mixed alcohol stream.

Another embodiment of the present invention is directed to a process for producing alcohols. In this embodiment, the invention includes a step of contacting a first syngas stream comprising carbon monoxide and hydrogen with a methanol synthesis catalyst in a methanol synthesis zone under first conditions effective to form a methanol-containing stream comprising hydrogen, carbon monoxide, methanol and water. A second syngas stream comprising carbon monoxide and optionally hydrogen contacts a methanol-containing feed stream and a homologation catalyst in a homologation zone under second conditions effective to form an ethanol-containing stream comprising carbon monoxide, methanol, ethanol, water and optionally hydrogen. At least a portion of the methanol-containing stream is combined with at least a portion of the ethanol-containing stream to form a combined stream. At least a portion of the combined stream is separated in a light ends removal unit into a first fraction and a second fraction. The first fraction comprises a weight majority of the hydrogen and carbon monoxide present in the at least a portion of the combined stream. The second fraction comprises a weight majority of the methanol, ethanol, and water present in the at least a portion of the combined stream. Water is removed from at least a portion of the second fraction in a water removal unit to form a third fraction and a fourth fraction. The third fraction comprises a weight majority of the methanol and ethanol present in the at least a portion of the second fraction. The fourth fraction comprises a weight majority of the water present in the at least a portion of the second fraction. The third fraction is separated into the methanol-containing feed stream and a final product stream, wherein the final product stream comprises methanol and ethanol. Optionally, the methanol-containing feed stream and the final product stream are aliquot portions of the third fraction, and the methanol-containing feed stream comprises methanol and ethanol. Optionally, this inventive process further comprises a step of contacting at least a portion of the final product stream with a molecular sieve catalyst composition under third conditions effective to convert the methanol and ethanol to light olefins. Optionally, the process further includes a step of separating the final mixed alcohol stream into a fifth fraction and a sixth fraction. The fifth fraction comprises a weight majority of the methanol present in the final mixed alcohol stream, and the sixth fraction comprises a weight majority of the ethanol present in the final mixed alcohol stream. Optionally, at least a portion of the fifth fraction contacts a molecular sieve catalyst composition under third conditions effective to convert the methanol contained therein into light olefins. Additionally or alternatively, at least a portion of the sixth fraction contacts a molecular sieve catalyst composition under third conditions effective to convert the ethanol contained therein to light olefins. Preferably, the step of contacting at a least a portion of the sixth fraction with a molecular sieve catalyst composition occurs in a fixed bed reaction system.

In another embodiment, the invention is directed to a process for producing light olefins. This process comprises a step of contacting a syngas stream comprising carbon monoxide, hydrogen and optionally carbon dioxide with a methanol synthesis catalyst under first conditions effective to form a methanol-containing stream comprising methanol and water. At least a portion of the methanol-containing stream contacts carbon monoxide, optionally hydrogen and a homologation catalyst under second conditions effective to form a mixed alcohol stream comprising methanol, ethanol, and water. At least a portion of the mixed alcohol stream contacts a molecular sieve catalyst composition in a reaction system under third conditions effective to convert the methanol and ethanol to light olefins. An effluent stream is yielded from the reaction system and comprises an ethylene to propylene weight ratio from about 0.9:1.0 to about 2.2:1.0, preferably from about 1.1:1.0 to about 1.4:1.0.

In one embodiment, the invention comprises a step of contacting a first syngas stream comprising carbon monoxide, hydrogen and optionally carbon dioxide with a methanol synthesis catalyst in a methanol synthesis zone under first conditions effective to form a methanol-containing stream comprising hydrogen, carbon monoxide, methanol and water. A second syngas stream comprising carbon monoxide and optionally hydrogen contacts a methanol-containing feed stream and a homologation catalyst in a homologation zone under second conditions effective to form an ethanol-containing stream comprising carbon monoxide, methanol, ethanol, water and optionally hydrogen. At least a portion of the methanol-containing stream is combined with at least a portion of the ethanol-containing stream to form a combined stream. At least a portion of the carbon monoxide, water and hydrogen are removed from at least a portion of the combined stream to form a final mixed alcohol stream. A first portion of the final mixed alcohol stream is directed to the homologation zone to serve as the methanol-containing feed stream. A second portion of the final mixed alcohol stream contacts a molecular sieve catalyst composition in a reaction system under third conditions effective to convert the methanol and ethanol to light olefins. An effluent stream, which has an ethylene to propylene weight ratio of from about 0.9:1.0 to about 2.2:1.0, preferably from about 1.1:1.0 to about 1.4:1.0, is yielded from the reaction system. The first portion of the final mixed alcohol stream and the second portion of the final mixed alcohol stream optionally are aliquot portions of the final mixed alcohol stream. The methanol-containing feed stream optionally comprises methanol and ethanol. Optionally, this inventive process further comprises a step of separating the final mixed alcohol stream into a first fraction and a second fraction. The first fraction comprises a weight majority of the methanol present in the final mixed alcohol stream, and the second fraction comprises a weight majority of the ethanol present in the final mixed alcohol stream. In this embodiment, the first portion of the final mixed alcohol stream optionally comprises a first portion of the first fraction. Optionally, the reaction system comprises a fast-fluidized reaction zone and a fixed bed reaction zone. A second portion of the first fraction is directed to the fast fluidized reaction zone for conversion of the methanol contained therein to light olefins. At least a portion of the second fraction is directed to the fixed bed reaction system for the conversion of the ethanol contained therein to light olefins.

BRIEF DESCRIPTION OF THE DRAWINGS

This invention will be better understood by reference to the detailed description of the invention when taken together with the attached drawings, wherein.

DETAILED DESCRIPTION OF THE INVENTION

A. Introduction

Figure 1:
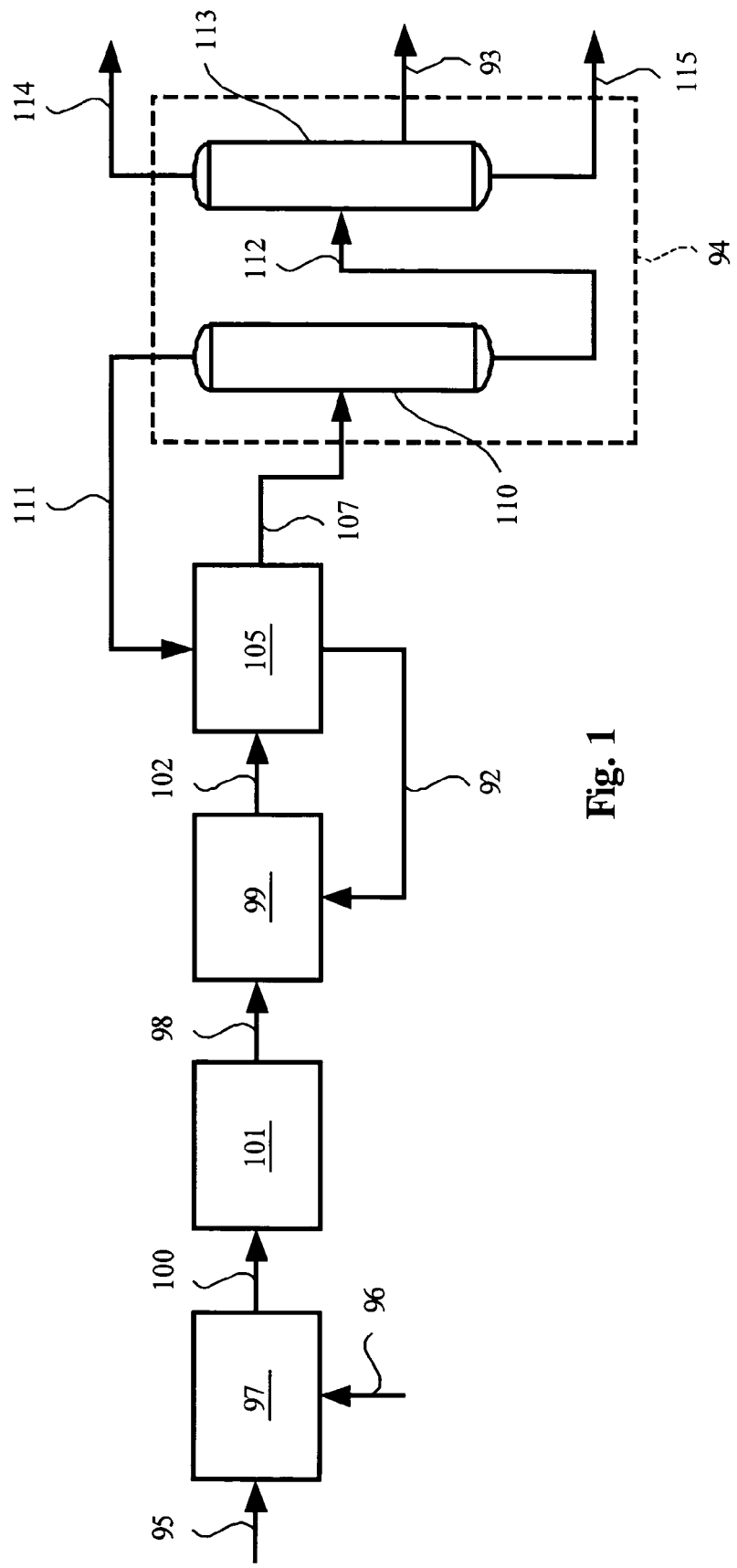
FIG. 1 is a flow diagram of a methanol synthesis system.

The present invention provides processes for forming an alcohol-containing stream comprising both methanol and ethanol. The methanol in the alcohol-containing stream is formed in a process for converting syngas to methanol in the presence of a catalyst composition. The ethanol in the alcohol-containing stream is formed from a homologation reaction of methanol with carbn monoxide and optionally hydrogen in the presence of a homologation catalyst. The alcohol-containing stream preferably is directed to an oxygenate to olefin (OTO) reaction system, wherein the methanol and ethanol contained in the alcohol-containing stream are converted to ethylene and propylene. According to one preferred embodiment of the present invention, the resulting weight ratio of ethylene to propylene that is formed in the OTO reaction system can be varied by varying the weight ratio of the methanol to ethanol contained in the alcohol-containing stream that is directed to the OTO reaction system, or by varying reaction conditions, e.g., temperature. Thus, the present invention is directed to an integrated system wherein methanol is synthesized in a methanol synthesis unit, and ethanol is synthesized in an ethanol synthesis unit. Preferably the methanol and the ethanol are combined to form a combined stream, which is directed to an OTO reaction system for the formation of ethylene and propylene. A detailed description of methanol synthesis systems will now be described.

B. Methanol Synthesis Systems

1. Examples of Methanol Synthesis Processes

There are numerous technologies available for producing methanol including fermentation or the reaction of synthesis gas (syngas) derived from a hydrocarbon feed stream, which may include natural gas, petroleum liquids, carbonaceous materials including coal, recycled plastics, municipal waste or any other organic material. Methanol is typically synthesized from the catalytic reaction of syngas in a methanol synthesis reactor in the presence of a heterogeneous catalyst. For example, in one synthesis process methanol is produced using a copper/zinc oxide catalyst in a water-cooled tubular methanol reactor. Syngas is defined as a gas comprising carbon monoxide (CO), preferably hydrogen ($H_2$) and optionally carbon dioxide ($CO_2$). Optionally, syngas may also include unreacted feedstocks such as methane ($CH_4$), ethane, propane, heavier hydrocarbons, or other compounds. Generally, the production of syngas involves a reforming reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol compositions can be manufactured from a hydrocarbon feed stream derived from a variety of carbon sources. Examples of such sources include biomass, natural gas, C1–C5 hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

One way of converting the carbon source to a methanol composition is to first convert the carbon source to syngas, and then convert the syngas to the methanol composition. Any conventional process can be used. In particular, any conventional carbon oxide conversion catalyst can be used to convert the syngas to the methanol composition. In one embodiment, the carbon oxide conversion catalyst is a nickel containing catalyst.

The hydrocarbon feed stream that is used in the conversion of hydrocarbon to syngas is optionally treated to remove impurities that can cause problems in further processing of the hydrocarbon feed stream. These impurities can poison many conventional propylene and ethylene forming catalysts. A majority of the impurities that may be present can be removed in any conventional manner. The hydrocarbon feed is preferably purified to remove sulfur compounds, nitrogen compounds, particulate matter, other condensables, and/or other potential catalyst poisons prior to being converted into syngas.

In one embodiment of the invention, the hydrocarbon feed stream is passed to a syngas plant. The syngas preferably has an appropriate molar ratio of hydrogen to carbon oxide (carbon monoxide and/or carbon dioxide), as described below. The syngas plant may employ any conventional means of producing syngas, including partial oxidation, steam or $CO_2$ reforming, or a combination of these two chemistries.

Steam reforming generally comprises contacting a hydrocarbon with steam to form syngas. The process preferably includes the use of a catalyst.

Partial oxidation generally comprises contacting a hydrocarbon with oxygen or an oxygen-containing gas such as air to form syngas. Partial oxidation takes place with or without the use of a catalyst, although the use of a catalyst is preferred. In one embodiment, water (steam) is added with the feed in the partial oxidation process. Such an embodiment is generally referred to as autothermal reforming.

Conventional syngas-generating processes include gas phase partial oxidation, autothermal reforming, fluid bed syngas generation, catalytic partial oxidation and various processes for steam reforming.

2. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \leftrightarrows CO + 3H_2 \tag{1}$$

or $$C_nH_m + nH_2O \leftrightarrows nCO + [n+(m/2)]H_2 \text{ and} \tag{2}$$

$$CO + H_2O \leftrightarrows CO_2 + H_2 \text{ (shift reaction)} \tag{3}$$

The reaction is carried out in the presence of a catalyst. Any conventional reforming type catalyst can be used. The catalyst used in the step of catalytic steam reforming comprises at least one active metal or metal oxide of Group 6 or Group 8–10 of the Periodic Table of the Elements. The Periodic Table of the Elements referred to herein is that from CRC Handbook of Chemistry and Physics, 82nd Edition, 2001–2002, CRC Press LLC, which is incorporated herein by reference.

In one embodiment, the catalyst contains at least one Group 6 or Group 8–10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with at least one promoter. Examples of promoters include alkali and rare earth promoters. Generally, promoted nickel oxide catalysts are preferred.

The amount of Group 6 or Group 8–10 metals in the catalyst can vary. Preferably, the catalyst includes from about 3 wt % to about 40 wt % of at least one Group 6 or Group 8–10 metal, based on total weight of the catalyst. Preferably, the catalyst includes from about 5 wt % to about 25 wt % of at least one Group 6 or Group 8–10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1 weight percent metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w as metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the syngas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, Encyclopedia of Chemical Technology, 3rd Ed., 1990, vol. 12, p. 951; and Ullmann's Encyclopedia of Industrial Chemistry, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

Typically, the syngas formed comprises hydrogen and a carbon oxide. The hydrogen to carbon oxide ratio of the syngas produced will vary depending on the overall conditions of the reformer. Preferably, the molar ratio of hydrogen to carbon oxide in the syngas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

3. Partial Oxidation to Make Syngas

The invention optionally provides for the production of syngas, or CO and $H_2$, by oxidative conversion (also referred to herein as partial oxidation) of hydrocarbons, particularly natural gas and $C_1$–$C_5$ hydrocarbons. According to the process, one or more hydrocarbons are reacted with free-oxygen to form CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \leftrightharpoons nCO + (m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Tl, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Tb, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminum titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about 103 $cm^3$/g·hr to about 105 $cm^3$/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O \rightleftharpoons H_2+CO_2$. This reaction occurs simultaneously with the oxidative conversion of the hydrocarbon in the feed to CO and $H_2$ or syngas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

4. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two syngas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form syngas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

In one embodiment, a gaseous mixture of hydrocarbon feedstock and oxygen-containing gas are contacted with a reforming catalyst under adiabatic conditions. For the purposes of this invention, the term "adiabatic" refers to reaction conditions in which substantially all heat loss and radiation from the reaction zone are prevented, with the exception of heat leaving in the gaseous effluent stream of the reactor.

5. Converting Syngas to Methanol

The syngas is sent to a methanol synthesis process and converted to methanol. The methanol synthesis process is accomplished in the presence of a methanol synthesis catalyst.

In one embodiment, the syngas is sent as is to the methanol synthesis process. In another embodiment, the hydrogen, carbon monoxide, and/or carbon dioxide content of the syngas is adjusted for efficiency of conversion. Desirably, the syngas input to the methanol synthesis reactor has a molar ratio of hydrogen ($H_2$) to carbon oxides (CO+$CO_2$) in the range of from about 0.5:1 to about 20:1, preferably in the range of from about 2:1 to about 10:1. In another embodiment, the syngas has a molar ratio of hydrogen ($H_2$) to carbon monoxide (CO) of at least 2:1. Carbon dioxide is optionally present in an amount of not greater than 50% by weight, based on total weight of the syngas.

Desirably, the stoichiometric molar ratio is sufficiently high so as maintain a high yield of methanol, but not so high as to reduce the volume productivity of methanol. Preferably, the syngas fed to the methanol synthesis has a stoichiometric molar ratio (i.e., a molar ratio of $H_2$:(2CO+3$CO_2$)) of from about 1.0:1 to about 2.7:1, more preferably from about 1.1 to about 2.0, more preferably a stoichiometric molar ratio of from about 1.2:1 to about 1.8:1.

The $CO_2$ content, relative to that of CO, in the syngas should be high enough so as to maintain an appropriately high reaction temperature and to minimize the amount of undesirable by-products such as paraffins. At the same time, the relative $CO_2$ to CO content should not be too high so as to reduce methanol yield. Desirably, the syngas contains $CO_2$ and CO at a molar ratio of from about 0.5 to about 1.2, preferably from about 0.6 to about 1.0.

In one embodiment, the catalyst used in the methanol synthesis process includes an oxide of at least one element selected from the group consisting of copper, silver, zinc, boron, magnesium, aluminum, vanadium, chromium, manganese, gallium, palladium, osmium and zirconium. Preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

The methanol synthesis catalyst is made according to conventional processes. Examples of such processes can be found in U.S. Pat. Nos. 6,114,279; 6,054,497; 5,767,039; 5,045,520; 5,254,520; 5,610,202; 4,666,945; 4,455,394; 4,565,803; 5,385,949, with the descriptions of each being fully incorporated herein by reference.

In one embodiment, the syngas formed in the syngas conversion plant is cooled prior to being sent to the methanol synthesis reactor. Preferably, the syngas is cooled so as to condense at least a portion of the water vapor formed during the syngas process.

The methanol synthesis process implemented in the present invention can be any conventional methanol synthesis process. Examples of such processes include batch processes and continuous processes. Continuous processes are preferred. Tubular bed processes and fluidized bed processes are particularly preferred types of continuous processes.

In general, the methanol synthesis process takes place according to the following reactions:

$$CO + 2H_2 \rightarrow CH_3OH \qquad (5)$$

$$CO_2 + 3H_2 \rightarrow CH_3OH + H_2O \qquad (6)$$

The methanol synthesis process is effective over a wide range of temperatures. In one embodiment, the syngas is contacted with the methanol synthesis catalyst at a temperature in the range of from about 302° F. (150° C.) to about 842° F. (450° C.), preferably in a range of from about 347° F. (175° C.) to about 662° F. (350° C.), more preferably in a range of from about 392° F. (200° C.) to about 572° F. (300° C.).

The process is also operable over a wide range of pressures. In one embodiment, the syngas is contacted with the methanol synthesis catalyst at a pressure in the range of from about 15 atmospheres to about 125 atmospheres, preferably in a range of from about 20 atmospheres to about 100 atmospheres, more preferably in a range of from about 25 atmospheres to about 75 atmospheres.

Gas hourly space velocities vary depending upon the type of continuous process that is used. Desirably, gas hourly space velocity of flow of gas through the catalyst bed is in the range of from about 50 hr-1 to about 50,000 hr-1. Preferably, gas hourly space velocity of flow of gas through the catalyst bed is in the range of from about 250 hr-1 to about 25,000 hr-1, more preferably from about 500 hr-1 to about 10,000 hr-1.

The methanol synthesis process produces a variety of hydrocarbons as by-products. According to the methanol composition of this invention, it is desirable to operate the process so as to maximize not only the amount of methanol formed, but also aldehydes and other alcohols which are particularly desirable in the conversion of oxygenates to olefins. In is particularly appropriate to maximize the amount of methanol formed in the methanol synthesis, and remove hydrocarbons less desirable in the conversion of oxygenates to olefins from the crude methanol product stream formed in the methanol synthesis reactor.

6. Refining Crude Methanol to Make Methanol Product

In conventional methanol synthesis systems, the crude methanol product mixture formed in the methanol synthesis unit is further processed after reaction to obtain a desirable methanol-containing composition. Processing is accomplished by any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol-containing composition, but without substantially reducing the amount of methanol and desirable aldehydes and/or other desirable alcohols also present.

In one processing system, the crude methanol product from the methanol synthesis reactor is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another processing system, the crude methanol is sent from the methanol synthesizing unit to a distillation system. The distillation system contains one or more distillation columns which are used to separate the desired methanol composition from water and hydrocarbon by-products. Desirably, the methanol composition that is separated from the crude methanol comprises a majority of the methanol and a majority of aldehyde and/or alcohol supplements contained in the crude alcohol prior to separation. Preferably, the methanol composition that is separated from the crude methanol comprises a majority of the acetaldehyde and/or ethanol, if any, contained in the crude methanol prior to separation.

The distillation system optionally includes a step of treating the methanol steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

The invention can include any distillation system that produces a "fusel oil" stream, which includes C1–C4 alcohols, aldehydes, ketones, esters and water. The fusel oil stream has a boiling point higher than that of methanol. It is especially advantageous when the fusel oil stream is liquid taken from a column fed with the crude methanol from the let-down vessel or with the bottoms liquid from a column fed with such crude methanol, the off-take point being at a level below the feed level. Alternatively or additionally, the fusel oil stream is taken from a level above the feed level in such a column. Because some of the higher alcohols are advantageous in the methanol composition of this invention, it is desirable to operate the distillation system to recover the $C_2$–$C_4$ alcohols along with the methanol rather than in the fusel oil stream.

Examples of distillation systems include the use of single and two column distillation columns. Preferably, the single columns operate to remove volatiles in the overhead, methanol product at a high level, fusel oil as vapor above the feed and/or as liquid below the feed, and water as a bottoms stream.

In one embodiment of a two column system, the first column is a "topping column" from which volatiles or "light ends" are taken overhead and methanol liquid as bottoms. A non-limiting list of possible light ends includes hydrogen, carbon monoxide and methane. The second is a "refining column" from which methanol product is taken as an overhead stream or at a high level, and water is removed as a bottoms stream. In this embodiment, the refining column includes at least one off-take for fusel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fusel oil side off-takes.

In yet another embodiment, the distillation system is one in which an aqueous, semi-crude methanol is taken as liquid above the feed in a single or refining column. The semi-crude methanol is passed to a refining column, from which methanol product is taken overhead or at a high level. Preferably, water or aqueous methanol is taken as a bottoms stream.

Alternatively, undesirable by-products are removed from the crude methanol stream from the methanol synthesis reactor by adsorption. In such a system, fusel oil can be recovered by regenerating the adsorbent.

An exemplary methanol synthesis system is illustrated in FIG. 1 and will now be described in greater detail. As shown in FIG. 1, a feed stream 95, which preferably includes natural gas, is directed to a desulfurization unit 97. Prior to entering the desulfurization unit 97, the feed stream 95 optionally is compressed by one or more compressors, not shown, to facilitate movement of the feed stream 95 and various intermediate streams through the methanol synthesis system. In one embodiment, the natural gas from feed stream 95 contacts water from water stream 96 in the desulfurization unit 97 in a countercurrent manner under conditions effective to remove sulfur-containing components, e.g., $H_2S$ and/or mercaptans, therefrom. In this manner, the desulfurization unit 97 acts as an absorption unit. Additionally or alternatively, the desulfurization unit 97 may act as an adsorption unit. In this embodiment, the desulfurization unit 97 preferably includes one or more columns that are packed with molecular sieve particles, e.g., 3–5 angstrom molecular sieve particles, the pores of which are adapted to selectively capture the sulfur-containing components from natural gas stream 95. The optional adsorption unit optionally includes a regeneration system, not shown, for regenerating deactivated or partially deactivated molecular sieve particles. If the desulfurization unit 97 includes an adsorption unit, the feed stream 95 preferably is heated to a temperature of between 700° F. (371° C.) and 800° F. (427°

C.) by a heat exchanger, not shown, before it is directed to desulfurization unit 97. The desulfurization unit 97 forms desulfurized feed stream 100, which is directed to a reforming unit 101. Preferably, desulfurized feed stream 100 comprises less than 5 weight percent, more preferably less than 1 weight percent, and most preferably less than 0.01 weight percent sulfur-containing compounds, based on the total weight of the desulfurized feed stream 100.

The reforming unit 101 converts the natural gas in desulfurized feed stream 100 to syngas in syngas stream 98. Generally, the production of syngas involves a combustion reaction of natural gas, mostly methane, and an oxygen source, e.g., air, into hydrogen, carbon monoxide and/or carbon dioxide. Syngas production processes are well known, and include conventional steam reforming, autothermal reforming, or a combination thereof. Thus, reforming unit 101 may be a steam reforming unit, a partial oxidation unit, an autothermal reforming unit, and/or a combined reforming unit, e.g., a unit that combines two or more of these reforming processes. In one embodiment, water from water stream 96 preferably increases the water content of, and more preferably saturates, the feed stream 95, in the process of removing sulfur-containing components. Additionally or alternatively, the desulfurized feed stream 100 is directed to a separate saturation unit, not shown, in which water contacts the desulfurized feed stream 100 under conditions effective to saturate the desulfurized feed stream 100 or increase the water content thereof. For example, the saturation unit may include a packed or tray column wherein water contacts the desulfurized feed stream 100 in a countercurrent manner under conditions effective to saturate or increase the water content of the desulfurized feed stream 100. Saturation of the feed stream 95 and/or desulfurized feed stream 100 is particularly beneficial if the reforming unit 101 implements a steam reforming process as a water-containing or saturated desulfurized feed stream 100 may be necessary in order for the steam reforming process to convert the desulfurized feed stream 100 to syngas in syngas stream 98. Additionally or alternatively, water may be injected directly into the reforming unit 101, particularly if the reforming unit 101 provides a steam reforming process. Resulting syngas stream 98 is directed to a compression zone 99, wherein the syngas stream 98 is compressed in one or more stages to form compressed stream 102. Preferably, the compression zone 99 includes one or more centrifugal compressors. Compressed stream 102 is then directed to a methanol synthesis unit 105, wherein the syngas in compressed stream 102 contacts a methanol synthesis catalyst under conditions effective to convert at least a portion of the syngas to crude methanol in crude methanol stream 107. Optionally, unreacted syngas from methanol synthesis unit 105 is recycled to compression zone 99 as shown by unreacted syngas stream 92.

The crude methanol in crude methanol stream 107 includes light ends, methanol, water, and fuel oil. Preferably, prior to introduction into separation zone 94, the crude methanol stream 107 is treated with a caustic medium, not shown, in a caustic wash unit, not shown, under conditions effective to increase the pH of the crude methanol stream 107. As a result, the crude methanol stream 107 also optionally includes dissolved caustic salts. As shown, crude methanol stream 107 is directed to a separation zone 94, which is adapted to separate one or more of these components and isolate a relatively pure methanol stream. The separation zone 94 includes a light ends separation unit 110, such as a topping column, and a refining column 113. Crude methanol stream 107 is first directed to the light ends separation unit 110, wherein conditions are effective to separate the crude methanol stream 107 into light ends stream 111 and bottoms crude methanol stream 112, which contains methanol, water, fusel oil, and optionally dissolved caustic salts. The light ends separation unit 110 typically includes from about 50 to about 80 trays and has a cross-sectional diameter of from about 8 feet (2.4 m) to about 20 feet (6 m). At least a portion of the light ends stream 111 preferably is recycled to methanol synthesis unit 105, as shown, for further conversion to methanol while the bottoms crude methanol stream 112 is directed to refining column 113 for further processing. In refining column 113, the bottoms crude methanol stream 112 is subjected to conditions effective to separate the bottoms crude methanol stream 112 into a refined methanol stream 114, a fusel oil stream 93, and a water stream 115. A majority of the caustic salts, if any, from bottoms crude methanol stream 112 are dissolved in water stream 115. Preferably, refined methanol stream 114 contains at least 95.0 weight percent, more preferably at least 99.0 weight percent and most preferably at least 99.5 weight percent methanol, based on the total weight of the refined methanol stream 114. Preferably, refined methanol stream 114 contains less than 0.25 weight percent, more preferably less than 1 weight percent and most preferably less than 5 weight percent water, based on the total weight of the refined methanol stream 114. The refining column 113 typically includes from about 80 to about 120 trays and has a cross-sectional diameter of from about 10 feet (3.0 m) to about 24 feet (7.2 m).

C. Ethanol Synthesis Systems

As indicated above, the present invention, in one embodiment, provides for a combined process for forming methanol and ethanol and converting the methanol and ethanol to light olefins in an OTO reaction system. A non-limiting description of several ethanol synthesis systems that may be incorporated into the present invention will now be described.

As with methanol synthesis, there are numerous technologies available for producing ethanol. The preferred embodiment for forming ethanol according to the present invention comprises the reaction of methanol, carbon monoxide, and optionally hydrogen in the presence of a catalyst composition to form ethanol and water. This reaction is typically referred to as a homologation reaction, and may be illustrated as follows:

$$CH_3OH+CO+2H_2 \rightarrow CH_3CH_2OH+H_2O \qquad (7)$$

According to the present invention, the homologation reaction optionally is catalyzed using a group VII transition metal compound as catalyst and a halogen as the promoter. Many other metal compounds and promoters, however, can be used. Optionally, secondary activators or ligands may be used in conjunction with the metal catalysts and promoters. These secondary activators can be other metallic salts or compounds, amines, phosphorus compounds, as well as a multitude of other compounds that have been disclosed in the published literature. Thus, a typical catalyst system for the homologation of methanol to ethanol comprises a metal atom-containing catalyst, a promoter and optionally ligands, solvents and/or secondary activators.

A variety of references disclose the homologation of methanol to ethanol. For example, U.S. Pat. No. 4,133,966 to Pretzer et al., the entirety of which is incorporated herein by reference, discloses a process for the homologation of methanol to ethanol using a catalyst system containing cobalt, acetylacetonate, a trivalent phosphorus or trivalent arsenic or trivalent antimony organic ligand, an iodine compound and a ruthenium compound. U.S. Pat. No. 4,111,837 to Taylor, the entirety of which is incorporated herein by reference, relates to the use of a heterogeneous co-catalyst system for the homologation of alkanols. The co-catalyst system contains cobalt, and rhenium metal. In U.S. Pat. No. 4,233,466 and U.S. Pat. No. 4,253,987, the entireties of which are both incorporated herein by reference, both to Fiato, there are disclosed processes and catalysts for the production of ethanol by the homologation reaction of methanol and syngas using a system containing cobalt atoms, rhenium atoms, iodine atoms and a phosphine ligand. U.S. Pat. Nos. 4,239,924 and 4,239,925, both to Pretzer et al., the entireties of which are also incorporated herein by reference, disclose a process for selectively processing ethanol using a system containing a specifically defined cobalt tricarbonyl complex, an iodine compound, and a rhenium compound in the methanol homologation reaction. Specifically, the '924 patent discloses the use of aliphatic substituted complexes, while the '925 patent discloses aromatic substituted complexes. U.S. Pat. No. 4,324,927 to Gauthier-Lafaye, the entirety of which is incorporated herein by reference, describes a process for the homologation of methanol to produce ethanol using a system containing cobalt atoms, rhenium atoms, and both an alkyl halide and an ionic halide. U.S. Pat. No. 4,304,946 to Isogai, the entirety of which is incorporated herein by reference, describes the homologation of methanol to produce ethanol using a cobalt sulfide compound or a mixture of a cobalt sulfide compound and a nitrogen-containing and/or a phosphorus-containing compound. This system is free of iodine atoms. U.S. Pat. No. 4,328,379 to Devon, the entirety of which is incorporated herein by reference, describes the homologation of methanol to produce ethanol using a cobalt-iodine catalyst system in the presence of a perfluorocarboxylate anion. U.K. Patent Application GB 2,083,465A to Isogai, the entirety of which is incorporated herein by reference, discloses the homologation of methanol to produce ethanol using a heterogeneous catalyst system comprising cobalt phosphate as the main catalyst. The applicants also disclose the use of a Group VIII metal as co-catalyst. U.S. Pat. No. 4,954,665 to the Vidal, the entirety of which is incorporated herein by reference, is directed to a process for producing ethanol at high efficiency, selectivity and conversion rate. The process comprises a homologation reaction of methanol and carbon monoxide and hydrogen using a catalyst system containing an alkali metal atom, a cobalt atom, an iodine atom, and, optionally, a ruthenium atom as well as an organic tertiary amino compound. Other U.S. patents that describe producing ethanol (and/or higher alcohols) from methanol, e.g., via methanol homologation, include U.S. Pat. No. 4,954,665; U.S. Pat. No. 4,608,447; U.S. Pat. No. 4,825,013; U.S. Pat. No. 4,533,775; U.S. Pat. No. 4,540,836; U.S. Pat. No. 4,578,375; U.S. Pat. No. 4,476,326; U.S. Pat. No. 4,424,384; U.S. Pat. No. 4,451,678; U.S. Pat. No. 4,409,404; U.S. Pat. No. 4,346,020; U.S. Pat. No. 4,423,258; U.S. Pat. No. 4,423,257, U.S. Pat. No. 4,361,499; U.S. Pat. No. 4,370,507; and U.S. Pat. No. 4,352,946, the entireties of which are all incorporated herein by reference.

The homologation reaction may occur at a variety of reaction conditions. In one embodiment, the homologation reaction temperature in the homologation zone ranges from about 650° F. (343° C.) to about 300° F. (149° C.), preferably from about 600° F. (316° C.) to about 400° F. (204° C.), and most preferably from about 550° F. (288° C.)to about 450° F. (232° C.). The pressure in the homologation zone also may vary widely, although the pressure preferably is in the range of the pressure of the syngas that is directed to the methanol synthesis unit, discussed above. Optionally, the pressure in the homologation zone ranges from about 900 psia (6206 kpaa) to about 4,000 psia (27,580 kpaa), preferably from about 1,000 psia (6,895 kPaa) to about 2,000 psia (13,790 kPaa), and most preferably from about 1,200 psia (8,274 kpaa) to about 1,500 psia (10,343 kPaa).

Although many different homologation catalysts may be utilized in the homologation zone to facilitate conversion of the methanol contained therein to ethanol, the homologation catalyst preferably is selected from the group consisting of potassium oxides, cobalt-molybdenum sulfides, nickel-molybdenum sulfides and potassium carbonates.

Many soluble halides may be used as a promoter in the catalyst system although it is preferred that iodine or its derivatives, e.g., iodine ions, be so employed. Illustrative sources of iodide ions include elemental iodine; cobalt iodide; hydrogen iodide; the alkyl iodides having from 1 to 10 carbon atoms such as methyl iodide, ethyl iodide, propyl iodide, 2-ethyhexyl iodide, n-decyl iodide, and the like. Any other source of iodide that will ionize to form free iodide ions in the reaction medium can be used as the promoter. One can also employ any of the organic iodine compounds that will furnish iodide to the reaction medium. Further, one can use mixtures of iodine and/or iodide compounds, if so desired. The preferred source of the iodide is elemental iodine.

The concentration of acidic iodine atoms in the homologation reactor optionally is from about 0.000013 to about 1.6 moles per liter; preferably from about 0.026 to about 0.6 mole per liter.

The alkali metal atom component of the catalyst system can come from any of the known ionic compounds of the alkali metals sodium, potassium, lithium, rubidium and cesium. Preferred alkali metal atom components are derived from sodium salts and potassium salts. Illustrative sources thereof include sodium iodide, sodium bicarbonate, sodium carbonate, sodium nitrate, sodium nitrite, sodium sulfate, sodium bisulfate, sodium chromate, sodium permanganate, sodium chlorate, sodium persulfate, sodium tetraborate, sodium bromide, sodium chloride, sodium fluoride, sodium sulfite, sodium hypochlorite, as well as any other ionic salt of sodium. Rather than repeat the individual compound names, the corresponding potassium, lithium, rubidium and cesium salts are illustrative of useful ionic compounds.

The concentration of alkali metal atoms in the homologation reactor optionally is from about 0.00013 to about 1 mole per liter; preferably from about 0.07 to about 0.6 mole per liter.

As indicated, an organic tertiary amino compound of the general formula $R_3N$ optionally is present as a co-promoter in the system. The use of such additives is known, as are their identities, to those skilled in this art. In this formula R represents an organic moiety. The additive can serve as a catalyst stabilizer and/or to further enhance efficiency, conversion rate and selectivity, especially when the reaction is carried out at higher temperature. The additive also serves to inhibit equipment corrosion in some instances. However, the use of the additive is not mandatory and the reaction can be carried out without it.

A large number of organic amines is known to those skilled in the art as useful and any of these can be used provided they do not have an adverse effect on the reaction. Among those of particular utility are the tertiary amines such as trimethylamine, triethylamine, tri-n-butylamine, tri-t-butylamine, tri-2-ethylhexylamine, methyl dibutylamine, tri-dodecylamine, tristearylamine, ethyl dibutylamine, tricyclohexylamine, triphenylamine, tri(4-methoxyphenyl)amine, tri(p-chlorophenyl)-amine, dibutyl phenylamine, dipentyl cyclopentylamine, ethyl diphenylamine, trinaphthylamine tri-p-tolylamine, tri-benzylamine, tri(3-methylcyclohexyl) amine, as well as other tertiary amines. These organic amines and many others are known in the art. They can be used singly or, if one desires, in mixtures containing two or more ligands.

The concentration of the $R_3N$ ligand in the homologation reactor optionally varies from about 0.000013 to about 0.08 mole per liter; preferably from about 0.02 to about 0.04 mole per liter.

Preferably, hydrogen and carbon monoxide are present in the syngas that is directed to the homologation reactor. The molar ratio of $H_2:CO$ in the syngas that is directed to the homologation zone can vary from about 20:1 to about 1:20, from about 10:1 to about 1:10, and preferably from about 3:1 to about 1:3. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether, alkanols such as methanol and acid esters such as methyl acetate.

Higher alcohols and carboxylic acid esters may also be formed while carrying out the process of this invention. Most often these derivatives are n-propanol, methyl formate, methyl acetate, ethyl acetate, ethyl ether, etc. The major by-products of the process such as the higher molecular weight alcohols and carboxylic acid esters, are, of course, also useful compounds and major articles of commerce. The higher alcohols, the carboxylic acid esters and ethers can easily be separated from one another by conventional means, e.g., fractional distillation in vacuo, if desired.

The novel process of this invention can be conducted in a batch, semi-continuous or continuous fashion. The catalyst may be initially introduced into the homologation zone batchwise, or it may be continuously or intermittently introduced into such a zone during the course of the synthesis reaction. Operating conditions can be adjusted to optimize the formation of the ethanol product, and after recovery of the alcohol and other products, a fraction rich in the catalyst composition may then be recycled to the reaction zone, if desired, and additional products generated. Preferably, the homologation zone is in a fixed bed reactor.

As is known in this art, one can additionally have an inert solvent present in the reaction mixture. A wide variety of substantially inert solvents are useful in the process of this invention including hydrocarbon and oxygenated hydrocarbon solvents. Suitable oxygenated hydrocarbon solvents are compounds comprising carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3. oxygen atoms. The solvent preferably is substantially inert under reaction conditions, is relatively non-polar and has a normal boiling point of at least 65° C. at atmospheric pressure, and preferably, the solvent will have a boiling point greater than that of ethanol and other oxygen-containing reaction products so that recovery of the solvent by distillation is facilitated.

Preferred ester type solvents are the aliphatic and acylic carboxylic acid monoesters as exemplified by butyl acetate, methyl benzoate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acylic ketones such as 2-pentanone, butanone, acetophenone, etc. Ethers that may be utilized as solvents include cyclic, acyclic and heterocyclic materials. Preferred ethers are the heterocyclic ethers as illustrated by 1,4-dioxane and 1,3-dioxane. Other suitable ether solvents include isopropyl propyl ether, diethylene glycol dibutyl ether, dibutyl ether, ethyl butyl ether, diphenyl ether, heptyl phenyl ether, anisole, tetrahydrofuran, etc. The most useful solvents of all of the above groups include the ethers as represented by monocyclic, heterocyclic ethers such a 1,4-dioxane or p-dioxane, etc. Hydrocarbon solvents, such as hexane, heptane, decane, dodecane, tetradecane, etc. are also suitable solvents for use in this invention. In the practice of this invention, it is also possible to add a small amount of water to the solvent and still obtain satisfactory results.

The reaction time varies depending upon the reaction parameters, reactor size and charge, and the individual components employed at the specific process conditions.

D. OTO Reaction Systems

The present invention, in one embodiment, provides for combining a methanol synthesis system with a homologation unit and an OTO reaction system, which is discussed in more detail hereinafter. As used herein, "reaction system" means a system comprising a reaction zone, optionally a disengaging zone, optionally a catalyst regenerator, optionally a catalyst cooler and optionally a catalyst stripper.

Typically, molecular sieve catalysts have been used to convert oxygenate compounds to light olefins. Ideally, the molecular sieve catalyst composition comprises an alumina or a silica-alumina catalyst composition. Silicoaluminophosphate (SAPO) molecular sieve catalysts are particularly desirable in such conversion processes, because they are highly selective in the formation of ethylene and propylene. A non-limiting list of preferable SAPO molecular sieve catalyst compositions includes SAPO-17, SAPO-18, SAPO-34, SAPO-35, SAPO-44, the substituted forms thereof, and mixtures thereof. Preferably, the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

Although the present application is specifically directed to combining a methanol/ethanol synthesis system with an OTO reaction system, one or more additional components may be included in the feedstock that is directed to the OTO reaction system. For example, the feedstock that is directed to the OTO reaction system optionally contains, in addition to methanol and ethanol, one or more aliphatic-containing compounds such as alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and more preferably from 1 to 4 carbon atoms, and most preferably methanol.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more oxygenates in addition to methanol and ethanol or, more specifically, one or more organic compounds containing at least one oxygen atom. In the most preferred embodiment of the process of invention, the oxygenate in the feedstock (in addition to methanol and ethanol) comprises one or more alcohols, preferably aliphatic alcohols where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates, in addition to methanol and ethanol, include n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock comprises methanol, ethanol and one or more of DME, diethyl ether or a combination thereof.

The various feedstocks discussed above are converted primarily into one or more olefins. The olefins or olefin monomers produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomers include unsaturated monomers, diolefins having 4 to 18 carbon atoms, conjugated or nonconjugated dienes, polyenes, vinyl monomers and cyclic olefins.

In a preferred embodiment, the feedstock, which contains methanol and ethanol, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as an oxygenate to olefins (OTO) reaction process. In an OTO process, typically an oxygenated feedstock, most preferably a methanol- and ethanol-containing feedstock, is converted in the presence of a molecular sieve catalyst composition into one or more olefins, preferably and predominantly, ethylene and/or propylene, referred to herein as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr-1 to about 5000 hr-1, preferably from about 2 hr-1 to about 3000 hr-1, more preferably from about 5 hr-1 to about 1500 hr-1, and most preferably from about 10 hr-1 to about 1000 hr-1. In one preferred embodiment, the WHSV is greater than 20 hr-1, preferably the WHSV for conversion of a feedstock containing methanol, DME, or both, is in the range of from about 20 hr-1 to about 300 hr-1.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

E. Integrated Reaction System

As indicated above, in one embodiment, the present invention is directed to a process for forming an alcohol-containing stream, which comprises methanol and ethanol. The methanol is synthesized in a methanol synthesis unit, and the ethanol is synthesized in an ethanol synthesis unit, which preferably includes a homologation zone. The alcohol-containing stream is particularly suitable for use in an OTO reaction system. Thus, in one embodiment, the present invention is directed to a system for producing light olefins, which system comprises a methanol synthesis unit, an ethanol synthesis unit and an OTO reaction system.

In another embodiment, the invention is to a process for producing light olefins. The process includes a step of contacting syngas in the presence of one or more metal-containing catalyst to produce a first feedstock comprising methanol. A portion of the methanol is converted in a homologation zone to a second feedstock comprising ethanol. The second feedstock optionally also includes methanol. The first feedstock and the second feedstock are introduced to a process for converting the methanol and the ethanol in the presnet of a molecular sieve catalyst composition to light olefins.

Ideally, the first and second feedstocks are combined to form a combined feedstock before being introduced to the process for converting the methanol and the ethanol to light olefins. In this embodiment, the combined feedstock optionally comprises methanol, ethanol and water. A weight majority of the water preferably is removed from the combined feedstock before being introduced to the process for converting the methanol and the ethanol to light olefins.

The combined feedstock also may include light ends such as carbon monoxide, methane and hydrogen. If so, then the process preferably includes a step of removing the light ends from at least a portion of the combined feedstock.

As indicated above, the combined feedstock includes both methanol and ethanol. Ideally, the combined feedstock has a methanol to ethanol weight ratio of from about 4.0:1.0 to about 99.0:1.0, more preferably from about 9.0:1.0 to about 19.0:1.0.

In one embodiment of the present invention, the process of converting the methanol and the ethanol in the presence of a molecular sieve catalyst composition to the light olefins also produces carbon monoxide. In this embodiment, the carbon monoxide optionally is separated from the light olefins. The separated carbon monoxide then may be directed to the homologation zone to provide a carbon monoxide source for the step of converting a portion of the methanol to the second feedstock.

Similarly, in one embodiment of the present invention, the process of converting the methanol and the ethanol in the presence of a molecular sieve catalyst composition to the light olefins also produces hydrogen. In this embodiment, the hydrogen optionally is separated from the light olefins. The separated hydrogen then may be directed to the homologation zone to provide a hydrogen source for the step of converting a portion of the methanol to the second feedstock.

In another embodiment, the invention is to an integrated process for producing light olefins. In this aspect of the invention, syngas contacts one or more metal-containing catalysts to produce a first feedstock comprising methanol. A portion of the methanol preferably contacts carbon monoxide in the presence of a catalyst system to produce a second feedstock comprising ethanol. The first feedstock and the second feedstock, optionally in a combined stream, are introduced to a process for converting the methanol and the ethanol in the presence of a molecular sieve catalyst composition to the light olefins.

In another embodiment, the invention is directed to a process for producing light olefins, which includes a step of contacting a syngas stream with a methanol synthesis catalyst under first conditions effective to form a methanol-containing stream comprising methanol. At least a portion of the methanol-containing stream contacts carbon monoxide and a homologation catalyst under second conditions effective to form a mixed alcohol stream comprising methanol and ethanol. At least a portion of the mixed alcohol stream contacts a molecular sieve catalyst composition under third conditions effective to convert the methanol and the ethanol to the light olefins.

Optionally, the mixed alcohol stream further comprises water and the process further comprises the step of separating a weight majority of the water from the mixed alcohol stream. The second conditions optionally comprise a holomogation reaction temperature of from about 204° C. to about 316° C. Optionally, the process further comprises a step of separating the mixed alcohol stream into a first fraction and a second fraction. The first fraction comprises a weight majority of the methanol present in the mixed alcohol stream, and the second fraction comprises a weight majority of the ethanol present in the mixed alcohol stream.

Another embodiment of the present invention is directed to a process for producing alcohols. In this embodiment, the invention includes a step of contacting a first syngas stream comprising carbon monoxide and hydrogen with a methanol synthesis catalyst in a methanol synthesis zone under first conditions effective to form a methanol-containing stream comprising hydrogen, carbon monoxide, methanol and water. A second syngas stream comprising carbon monoxide and optionally hydrogen contacts a methanol-containing feed stream and a homologation catalyst in a homologation zone under second conditions effective to form an ethanol-containing stream comprising carbon monoxide, methanol, ethanol, water and optionally hydrogen. At least a portion of the methanol-containing stream is combined with at least a portion of the ethanol-containing stream to form a combined stream. At least a portion of the combined stream is separated in a light ends removal unit into a first fraction and a second fraction. The first fraction comprises a weight majority of the hydrogen and carbon monoxide present in the at least a portion of the combined stream. The second fraction comprises a weight majority of the methanol, ethanol, and water present in the at least a portion of the combined stream. Water is removed from at least a portion of the second fraction in a water removal unit to form a third fraction and a fourth fraction. The third fraction comprises a weight majority of the methanol and ethanol present in the at least a portion of the second fraction. The fourth fraction comprises a weight majority of the water present in the at least a portion of the second fraction. The third fraction is separated into the methanol-containing feed stream and a final product stream, wherein the final product stream comprises methanol and ethanol.

Optionally, the methanol-containing feed stream and the final product stream are aliquot portions of the third fraction, and the methanol-containing feed stream comprises methanol and ethanol. Optionally, this inventive process further comprises a step of contacting at least a portion of the final product stream with a molecular sieve catalyst composition under third conditions effective to convert the methanol and ethanol to light olefins. Optionally, the process further includes a step of separating the final mixed alcohol stream into a fifth fraction and a sixth fraction. The fifth fraction comprises a weight majority of the methanol present in the final mixed alcohol stream, and the sixth fraction comprises a weight majority of the ethanol present in the final mixed alcohol stream. Optionally, at least a portion of the fifth fraction contacts a molecular sieve catalyst composition under third conditions effective to convert the methanol contained therein into light olefins. Additionally or alternatively, at least a portion of the sixth fraction contacts a molecular sieve catalyst composition under third conditions effective to convert the ethanol contained therein to light olefins. Preferably, the step of contacting at a least a portion of the sixth fraction with a molecular sieve catalyst composition occurs in a fixed bed reaction system.

In another embodiment, the invention is directed to a process for producing light olefins. This process comprises a step of contacting a syngas stream comprising carbon monoxide, hydrogen and optionally carbon dioxide with a methanol synthesis catalyst under first conditions effective to form a methanol-containing stream comprising methanol and water. At least a portion of the methanol-containing stream contacts carbon monoxide, optionally hydrogen and a homologation catalyst under second conditions effective to form a mixed alcohol stream comprising methanol, ethanol, and water. At least a portion of the mixed alcohol stream contacts a molecular sieve catalyst composition in a reaction system under third conditions effective to convert the methanol and ethanol to light olefins. An effluent stream is yielded from the reaction system and comprises an ethylene to propylene weight ratio from about 0.9:1.0 to about 2.2:1.0, preferably from about 1.1:1.0 to about 1.4:1.0.

In one embodiment, the invention comprises a step of contacting a first syngas stream comprising carbon monoxide, hydrogen and optionally carbon dioxide with a methanol synthesis catalyst in a methanol synthesis zone under first conditions effective to form a methanol-containing stream comprising hydrogen, carbon monoxide, methanol and water. A second syngas stream comprising carbon monoxide and optionally hydrogen contacts a methanol-containing feed stream and a homologation catalyst in a homologation zone under second conditions effective to form an ethanol-containing stream comprising carbon monoxide, methanol, ethanol, water and optionally hydrogen. At least a portion of the methanol-containing stream is combined with at least a portion of the ethanol-containing stream to form a combined stream. At least a portion of the carbon monoxide, water and hydrogen are removed from at least a portion of the combined stream to form a final mixed alcohol stream. A first portion of the final mixed alcohol stream is directed to the homologation zone to serve as the methanol-containing feed stream. A second portion of the final mixed alcohol stream contacts a molecular sieve catalyst composition in a reaction system under third conditions effective to conver the methanol and ethanol to light olefins. An effluent stream, which has an ethylene to propylene weight ratio of from about 0.9:1.0 to about 2.2:1.0, preferably from about 1.1:1.0 to about 1.4:1.0, is yielded from the reaction system.

In this embodiment, the first portion of the final mixed alcohol stream and the second portion of the final mixed alcohol stream optionally are aliquot portions of the final mixed alcohol stream. The methanol-containing feed stream optionally comprises methanol and ethanol. Optionally, this inventive process further comprises a step of separating the final mixed alcohol stream into a first fraction and a second fraction. The first fraction comprises a weight majority of the methanol present in the final mixed alcohol stream, and the second fraction comprises a weight majority of the ethanol present in the final mixed alcohol stream. In this embodiment, the first portion of the final mixed alcohol stream optionally comprises a first portion of the first fraction. Optionally, the reaction system comprises a fast-fluidized reaction zone and a fixed bed reaction zone. A second portion of the first fraction is directed to the fast fluidized reaction zone for conversion of the methanol contained therein to light olefins. At least a portion of the second fraction is directed to the fixed bed reaction system for the conversion of the ethanol contained therein to light olefins.

Optionally, the homologation zone is made part of an existing methanol synthesis system. In this embodiment, the beds in the methanol synthesis unit preferably are replaced with beds suitable for the homologation reaction. Additionally or alternatively, a second ethanol synthesis unit having a homologation zone can be incorporated into a methanol synthesis system, as described below with reference to FIGS. 2–4.

Figure 2:
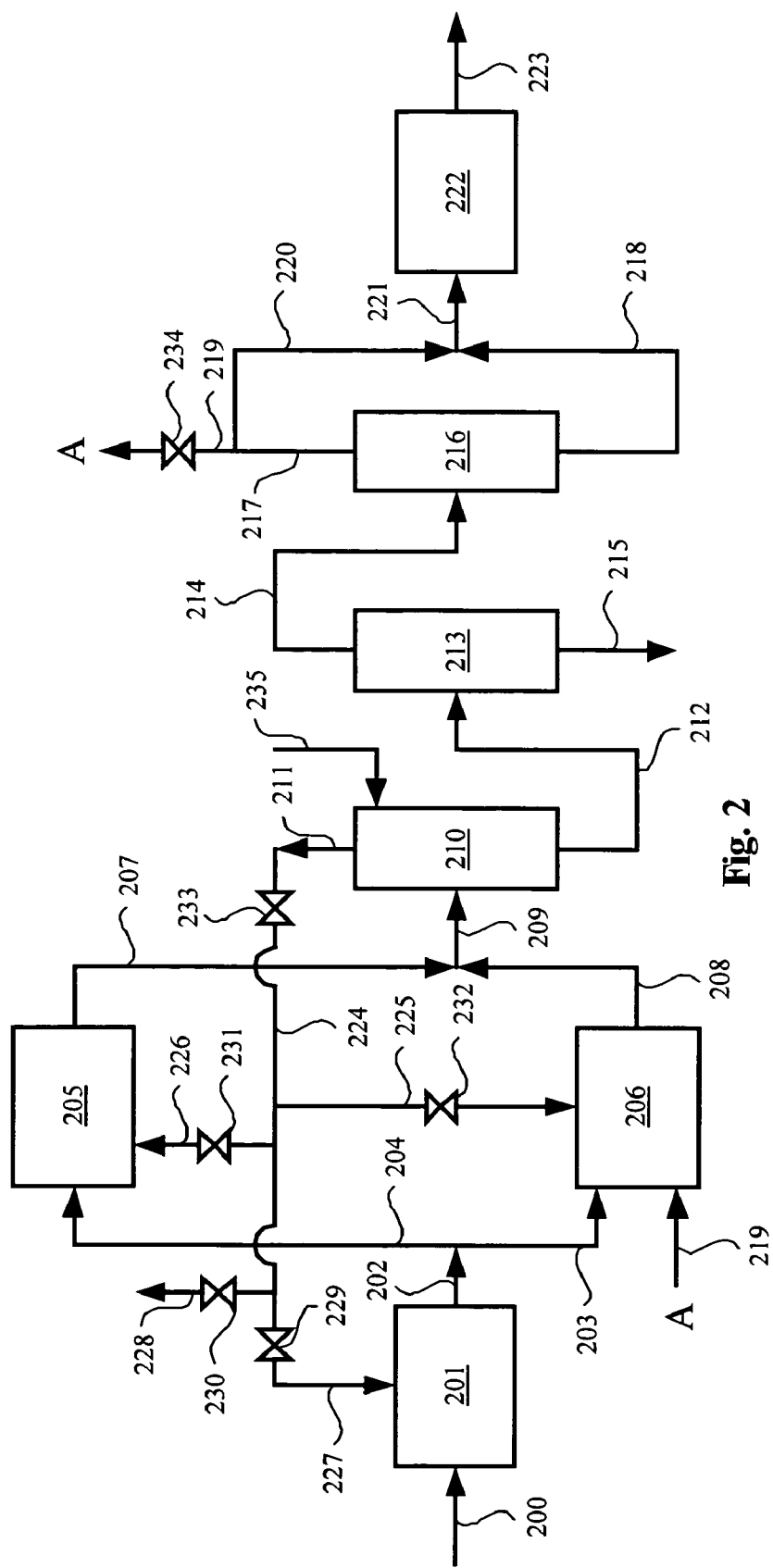
FIG. 2 is a flow diagram of one embodiment of the present invention.
Figure 3:
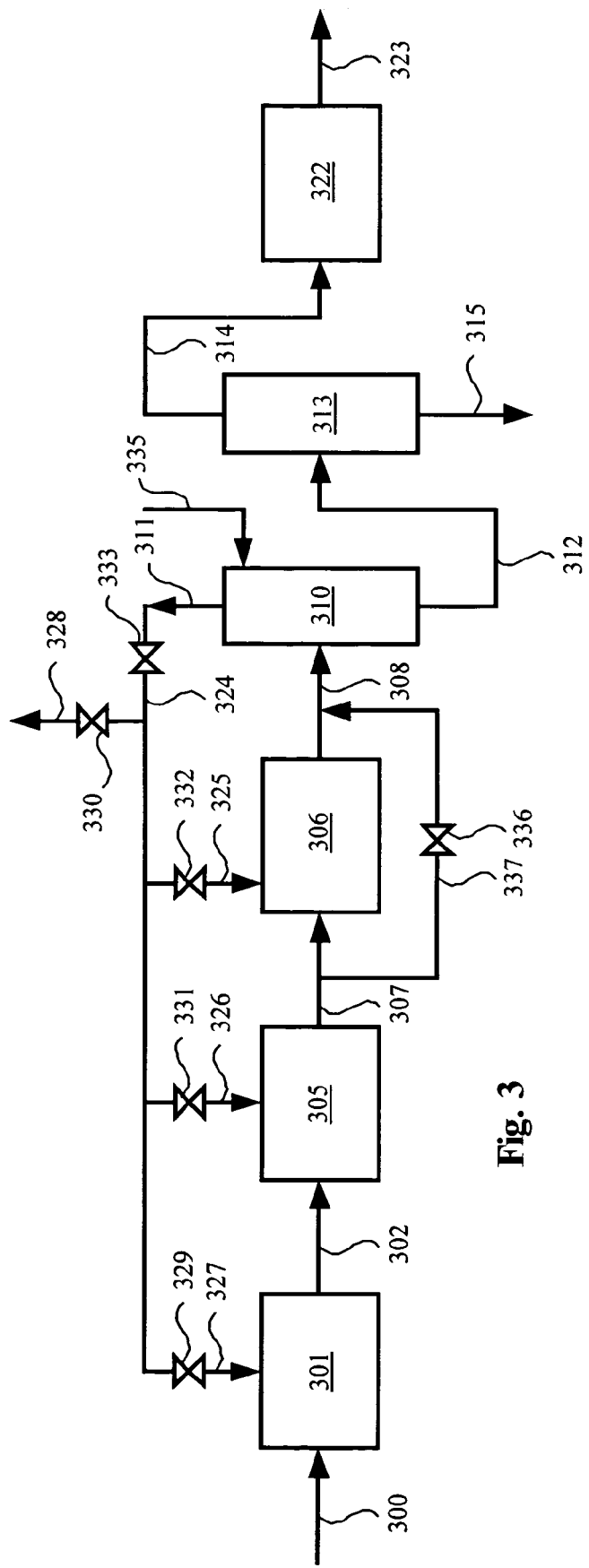
FIG. 3 is a flow diagram of another embodiment of the present invention.
Figure 4:
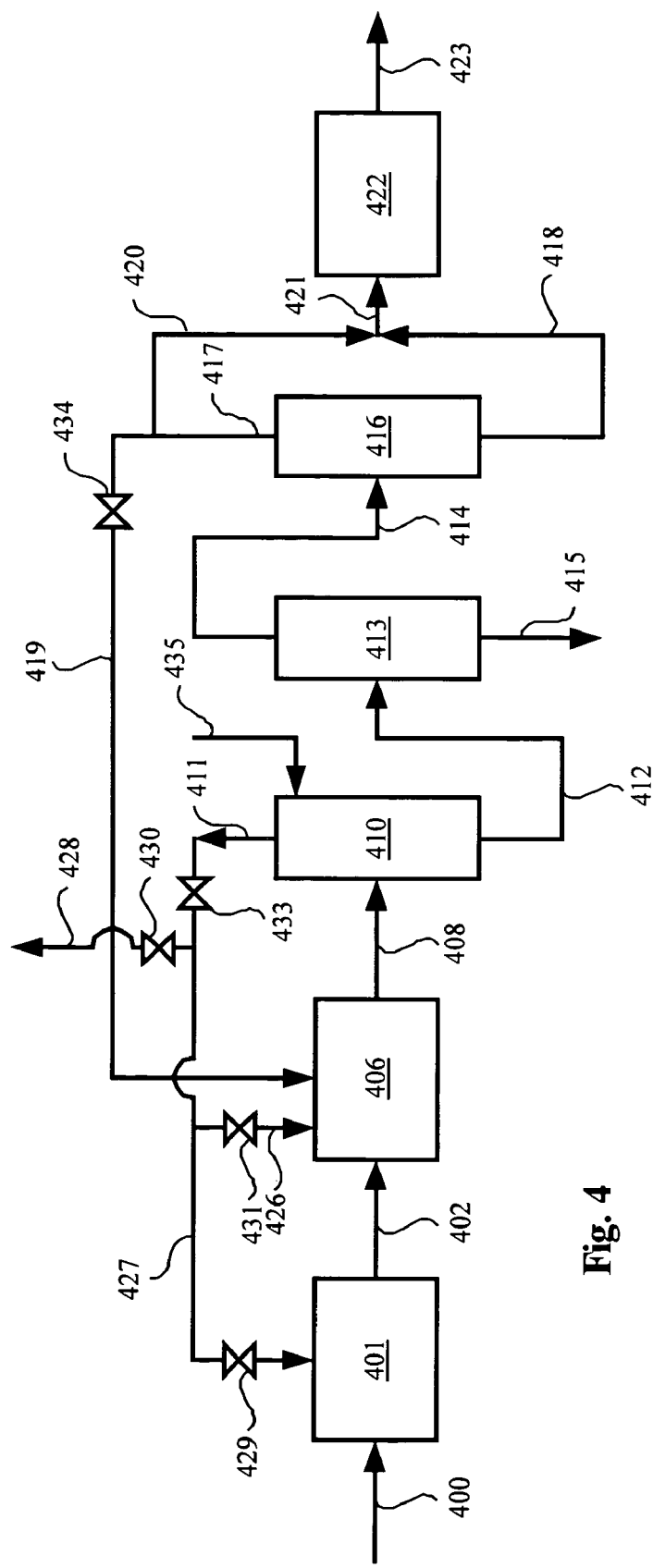
FIG. 4 is a flow diagram of another embodiment of the present invention.

FIGS. 2–4 of the present specification illustrate three non-limiting examples of integrated systems according to three embodiments of the present invention.

FIG. 2 illustrates one embodiment of the present invention wherein the methanol synthesis unit operates in parallel to the ethanol synthesis unit. As shown, a natural gas stream 200 comprising natural gas is directed to a syngas generation unit 201. Ideally, the natural gas stream 200 comprises less than 5 weight percent, more preferably less than 1 weight percent, and most preferably less than 0.01 weight percent sulfur-containing compounds, based on the total weight of the natural gas stream 200. In the syngas generation unit 201, the natural gas in natural gas stream 200 contacts oxygen under conditions effective to convert the natural gas into syngas, which is yielded from the syngas generation unit 201 in syngas stream 202. Generally, the production of syngas involves a combustion reaction of natural gas, mostly methane and an oxygen source, e.g., air, into hydrogen carbon monoxide and/or carbon dioxide. Syngas production process are well known, and include conventional steam reforming, autothermal reforming, or a combination thereof. Thus, syngas generation unit 201 may be a steam reforming unit, a partial oxidation unit, an autothermal reforming unit, and/or a combined reforming unit, e.g., a unit that combines two or more of these reforming processes. Optionally, water from a water stream, not shown, is added to the natural gas stream 200 or the syngas generation unit 201 in order to increase the water content of, and preferably saturate, the natural gas stream 200. Natural gas stream 200 optionally is desulfurized and/or saturated by any of the methods described above with reference to FIG. 1.

Syngas stream 202 ideally is compressed in one or more compressors, not shown, and is divided into a first derivative syngas stream 204 and a second derivative syngas stream 203. Optionally, the syngas in first derivative syngas stream 204 is compressed to provide ideal pressurization characteristics for methanol synthesis. Similarly, second derivative syngas stream 203 optionally is compressed to provide ideal pressurization characteristics for conversion thereof to ethanol in ethanol synthesis unit 206. First derivative syngas stream 204, or a portion thereof, is directed to a methanol synthesis unit 205 wherein the syngas in first derivative syngas stream 204 contacts a methanol synthesis catalyst under conditions effective to convert the syngas to methanol. Thus, methanol synthesis unit 205 yields a methanol-containing stream 207, which optionally comprises light ends, methanol, water, and fusel oil. Optionally, prior to the separation of the components contained in methanol-containing stream 207, the methanol-containing stream 207 is treated with a caustic medium, not shown, in a caustic wash unit, not shown, under conditions effective to increase the pH of the methanol-containing stream 207.

Meanwhile, second derivative syngas stream 203, or a portion thereof, is directed to ethanol synthesis unit 206, wherein the syngas in the second derivative syngas stream 203 contacts methanol and a homologation catalyst composition under conditions effective to form ethanol, which is yielded from the ethanol synthesis unit 206 in ethanol-containing stream 208. Additionally, ethanol-containing stream 208 optionally comprises methanol, light ends, water, 208 optionally is treated in a caustic wash unit, not shown, to increase the pH thereof. As shown in FIG. 2, the methanol-containing stream 207 is combined with the ethanol-containing stream 208 to form combined alcohol-containing stream 209.

Combined alcohol-containing stream 209 preferably is directed to a separation zone, which comprises a light ends separation unit 210, such as a topping column, and a refining column 213. In the light ends separation unit 210, conditions are effective to separate the combined alcohol-containing stream 209 into light ends stream 211 and bottoms alcohol stream 212.

At least a portion of light ends stream 211 preferably is recycled to one or more of the syngas generation unit 201, the methanol synthesis unit 205, and/or the ethanol synthesis unit 206. As shown, stream 224, the flow of which is regulated by flow control device 233, carries light ends from light ends stream 211 to one or more of these units. Specifically, stream 227 carries the light ends from stream 224 to the syngas generation unit 201. Similarly, stream 225 carries light ends from stream 224 to the ethanol synthesis unit 206. Likewise, stream 226 carries light ends from stream 224 to the methanol synthesis unit 205. The flow of the light ends through these various streams optionally is controlled via flow control devices 229, 232 and 231. As shown, a portion of the components in stream 224 can be removed from the system via purge stream 228. The flow rate at which components are removed from the system via purge stream 228 optionally is controlled via flow control device 230.

In one embodiment, the light ends separation unit 210 also functions as a caustic wash unit. As shown, a caustic stream 235 is introduced to the light ends separation unit 210 under conditions effective to increase the pH of the combined alcohol-containing stream 209 after it has been introduced therein. Thus, bottoms alcohol stream 212 may include caustic salts from caustic stream 235.

As shown, bottoms alcohol stream 212 is directed to refining column 213, wherein water and optionally fusel oil, not shown, are separated from the methanol and ethanol contained in bottoms alcohol stream 212. Thus, bottoms alcohol stream 212 is separated into a water-containing stream 215, a fusel oil stream, not shown, and a refined alcohol stream 214, which preferably, in this embodiment, is directed to a methanol concentrator 216. Water-containing stream 215 preferably contains a weight majority of the caustic salts that were contained in bottoms alcohol stream 212.

In methanol concentrator 216, refined alcohol stream 214 preferably is subjected to conditions effective to form methanol concentrated stream 217 and methanol diluted stream 218. Methanol concentrated stream 217 comprises a weight majority of the methanol contained in refined alcohol stream 214 and optionally a portion of the ethanol contained in refined alcohol stream 214. Conversely, methanol diluted stream 218 comprises a weight majority of the ethanol contained in refined alcohol stream 214 and optionally a portion of the methanol contained in refined alcohol stream 214. The purpose of the methanol concentrator is to form a stream concentrated in methanol (the methanol concentrated stream 217), a portion of which may be directed to the ethanol synthesis unit 206 to serve as a methanol source for the homologation reaction. As shown, methanol concentrated stream 217 is separated, preferably in aliquot portions, into recycle stream 219 and stream 220. Recycle stream 219 preferably is rich in methanol and is directed to ethanol synthesis unit 206 to serve as a methanol source for the homologation reaction occurring therein. The flow of the recycle stream 219 optionally is controlled via flow control device 234.

Stream 220, which is derived from methanol concentrated stream 217, preferably is combined with at least a portion of the methanol diluted stream 218 to form combined alcohol stream 221.

Combined alcohol stream 221, which comprises largely methanol and ethanol, is then directed to an OTO reactor 222 wherein the methanol and ethanol contained in the combined alcohol stream 221 contact one or more molecular sieve catalyst compositions under conditions effective to form ethylene and propylene, which are yielded from the OTO reactor 222 in light olefins containing stream 223.

In another embodiment, not shown, stream 220 is not combined with methanol diluted stream 218. Instead, stream 220 is directed to an MTO reactor, not shown, wherein the methanol contained in stream 220 contacts one or more molecular sieve catalyst compositions under conditions effective to convert the methanol contained therein to ethylene and propylene. In this embodiment, methanol diluted stream 218 optionally is directed to an ethanol to olefins (ETO) reactor, not shown, wherein the ethanol contained in methanol diluted stream 218 contacts one or more molecular sieve catalyst compositions under conditions effective to convert the ethanol contained therein to ethylene. In this embodiment, the reactor type and/or reaction conditions of the MTO and ETO reactors may differ from one another in order to provide optimized conditions for converting the methanol to light olefins in the MTO reactor and for converting the ethanol to ethylene in the ETO reactor.

FIG. 3 illustrates another embodiment of the present invention wherein the methanol synthesis unit and the ethanol synthesis unit are situated in series rather than in parallel. As shown, natural gas stream 300 comprising natural gas is directed to a syngas generation unit 301 wherein the natural gas is converted to syngas in syngas stream 302. Syngas generation unit 301 optionally comprises a steam reforming unit, a partial oxidation unit, an autothermal reforming unit, and/or a combined reforming unit, e.g., a unit that combines two or more of these reforming processes. As above, natural gas stream 300 optionally is saturated with water prior to or upon introduction into syngas generation unit 301. Syngas stream 302 preferably is directed to a compression zone, not shown, wherein the syngas stream 302 is compressed to a pressure favorable for conversion thereof to methanol. After compression, syngas stream 302 is directed to methanol synthesis unit 305 for conversion thereof to methanol. In the methanol synthesis unit, the syngas stream 302 contacts one or more methanol synthesis catalysts under conditions effective to convert at least a portion of the syngas to crude methanol, which is yielded from the methanol synthesis unit via methanol-containing stream 307. Optionally, unreacted syngas from methanol synthesis unit 305 is recycled to the compression zone.

Methanol-containing stream 307, which is yielded from the methanol synthesis unit 305, preferably comprises light ends, methanol, water and fusel oil. As shown, at least a portion of methanol-containing stream 307 is directed to an ethanol synthesis unit 306, which preferably comprises a homologation zone. In the ethanol synthesis unit 306, at least a portion of the methanol-containing stream 307 contacts carbon monoxide, preferably hydrogen, and optionally carbon dioxide in the presence of one or more homologation catalysts under conditions effective to form ethanol. The ethanol formed in ethanol synthesis unit 306 is yielded therefrom via ethanol-containing stream 308.

Depending on reaction conditions and the specific catalyst used in the ethanol synthesis unit 306, all or a portion of the methanol that was introduced into the ethanol synthesis unit 306 may be converted to ethanol. As it is desirable according to the present invention to provide an alcohol-containing stream that comprises both methanol and ethanol, a portion of the methanol from methanol-containing stream 307 optionally bypasses the ethanol synthesis unit 306, as shown by bypass stream 337, the flow of which is controlled by flow control device 336. Ideally, as shown in FIG. 3, bypass stream 337 is recombined with ethanol-containing stream 308 prior to the introduction thereof into the separation zone for removal of undesirable components therefrom.

As shown, ethanol-containing stream 308, which comprises methanol, ethanol, water, light ends, and fusel oil is introduced into light ends separation unit 310. In light ends separation unit 310, the light ends in ethanol-containing stream 308 are separated from the other components contained therein. Specifically, in light ends separation unit 310, the ethanol-containing stream 308 is subjected to conditions effective to form light ends stream 311 and bottoms alcohol stream 312. Light ends stream 311 preferably comprises a weight majority of the light ends that were contained in ethanol-containing stream 308, while the bottoms alcohol stream 312 comprises a weight majority of the methanol, ethanol, water and fusel oil present in the ethanol-containing stream 308.

Preferably, a portion of light ends stream 311 is directed through stream 324 to one or more of the syngas generation unit 301, the methanol synthesis unit 305, and/or the ethanol synthesis unit 306. As illustrated, stream 324 is directed to the syngas generation unit 301 via stream 327, to the methanol synthesis unit 305 via stream 326, and to the ethanol synthesis unit 306 via stream 325. The flow rate at which the light ends stream 311, or a portion thereof, is directed to these units may be varied by flow control devices 329, 331, 332, and/or 333. Preferably, a portion of the light ends are purged from the system via purge stream 328, the flow of which may be controlled by flow control device 330.

As indicated above, light ends separation unit 310 optionally also functions as a caustic wash unit. As shown, caustic stream 335 is introduced into light ends separation unit 310 under conditions effective to increase the pH of the bottoms alcohol stream 312. As a result, bottoms alcohol stream 312 optionally comprises caustic salts in addition to methanol, ethanol, water and fusel oil. As shown, bottoms alcohol stream 312 is directed to a refining column 313 for removal of the water contained therein. Thus, refining column 313 operates to separate the bottoms alcohol stream 312 into a refined alcohol stream 314 and a water-containing stream 315. Preferably, water-containing stream 315 comprises a weight majority of the water that was present in the bottoms alcohol stream 312. Similarly, refined alcohol stream 314 preferably comprises a weight majority of the methanol and ethanol contained in bottoms alcohol stream 312. Refining column 313 optionally also forms a side draw stream, not shown, whereby a weight majority of the fusel oil that was contained in bottoms alcohol stream 312 is removed therefrom. Refined alcohol stream 314, which comprises methanol and ethanol, may then be directed to an OTO reactor 322, wherein the methanol and ethanol contained therein are converted to light olefins, which are yielded from the OTO reactor 322 via light olefins containing stream 323.

FIG. 4 illustrates another embodiment of the present invention wherein methanol synthesis and ethanol synthesis occur in a single reaction zone. As shown, natural gas stream 400 comprising natural gas is directed to a syngas generation unit 401, which optionally comprises a steam reforming unit, a partial oxidation unit, an autothermal reforming unit, and/or a combined reforming unit. As with the above embodiments, water is optionally added to natural gas stream 400 and/or syngas generation unit 401 in order to increase the water content thereof. In syngas generation unit 401, the natural gas from natural gas stream 400 is converted to syngas, which is yielded from the syngas generation unit 401 via syngas stream 402.

Syngas stream 402 preferably is directed to a combined synthesis unit 406 wherein, at least initially, the syngas from syngas stream 402 contacts one or more catalyst compositions under conditions effective to form methanol and water, which are yielded from the combined synthesis unit 406 via alcohol stream 408. Combined synthesis unit 406 preferably also receives methanol from a methanol source. The methanol that is received in combined synthesis unit 406 preferably contacts carbon monoxide and preferably hydrogen as well as one or more homologation catalysts under conditions effective to form ethanol. Thus, combined synthesis unit 406 contains both a methanol synthesis catalyst and a homologation catalyst and operates to form both methanol and ethanol, which are yielded from the combined synthesis unit with water, light ends, and fusel oil via alcohol stream 408.

Alcohol stream 408 preferably is then directed to a separation zone. As shown, alcohol stream 408 is directed to a light ends separation unit 410, wherein the alcohol stream 408 is separated into a light ends stream 411 and a bottoms alcohol stream 412. Light ends stream 411 preferably comprises a weight majority of the light ends that were present in alcohol stream 408, while bottoms alcohol stream 412 preferably comprises a weight majority of the methanol, ethanol, fusel oil and water that was present in alcohol stream 408. Ideally, at least a portion of light ends stream 411 is recycled to one or more of the syngas generation unit 401 and/or the combined synthesis unit 406. As shown, stream 427 and stream 426 delivere the light ends to the syngas generation unit and the combined synthesis unit, respectively. The flow rate at which the light ends are delivered to these units optionally is controlled via flow control devices 429, 431 and 433. If recycle of the light ends is desired, then a portion of light ends stream 411 preferably is purged from the reaction system, as shown by purge stream 428. The flow rate at which undesirable components are removed from the reaction system optionally is controlled by flow control device 430.

As indicated above, light ends separation unit 410 optionally also functions as a caustic wash unit in order to increase the pH of the streams yielded therefrom. As shown, caustic stream 435 is introduced into light ends separation unit 410. As a result, bottoms alcohol stream 412 optionally comprises caustic salts in addition to methanol, ethanol, water and fusel oil.

Bottoms alcohol stream 412 is then directed to a refining column 413 wherein water and fusel oil are separated from the methanol and ethanol contained in bottoms alcohol stream 412. Specifically, upon introduction into refining column 413, bottoms alcohol stream 412 is subjected to conditions effective to form a refined alcohol stream 414 and a water-containing stream 415. Preferably water-containing stream 415 comprises a weight majority of the water contained in bottoms alcohol stream 412. Similarly, refined alcohol stream 414 preferably comprises a weight majority of the methanol and ethanol contained in bottoms alcohol stream 412. Additionally, a weight majority of the fusel oil contained in bottoms alcohol stream preferably is yielded from the refining column 413 via a side draw stream, not shown. In this embodiment, in order to provide a methanol source for the combined synthesis unit 406, all or a portion of refined alcohol stream 414 preferably is directed to a methanol concentrator 416. Upon introduction into methanol concentrator 416, the refined alcohol stream 414 is subjected to conditions effective to form methanol concentrated stream 417 and methanol diluted stream 418. Methanol concentrated stream 417 preferably comprises a weight majority of the methanol that was contained in the refined alcohol stream 414, while the methanol diluted stream 418 preferably comprises a weight majority of the ethanol contained in the refined alcohol stream 414.

A portion of methanol concentrated stream 417 preferably is then directed to the combined synthesis unit 406 as shown by recycle stream 419. The flow rate at which methanol is supplied to the combined synthesis unit 406 optionally is controlled by flow control device 434. The remaining portion of methanol concentrated stream 417, illustrated by stream 420, preferably is combined with methanol diluted stream 418 to form a combined alcohol stream 421. Combined alcohol stream 421 is then directed to an OTO reactor 422, wherein the methanol and ethanol contained in the combined alcohol stream 421 contact one or more molecular sieve catalyst compositions under conditions effective to form ethylene and propylene, which are yielded therefrom in light olefin-containing stream 423.

The reaction conditions in the combined synthesis unit 406 may vary widely. In one embodiment, the conditions include a pressure of about 1400 psig (9653 kPag), and a temperature ranging from 400° F. to 500° F. (204° C. to 260° C.). The feed gas composition that is directed to the combined synthesis unit 406 optionally comprises about 85 molar percent hydrogen, about 3 molar percent carbon monoxide, about 2 molar percent carbon dioxide and about 10 molar percent methane. At these conditions, homologation catalysts such as $K_2CO_2$/CoMo Sulfides will convert the synthesized methanol into ethanol. It has been found that even at high $H_2$/CO ratios, the amount of hydrocarbons (fully saturated, non-oxygenated) formed in the combined synthesis unit 406 at these conditions is acceptably low (about 2 weight percent at 550° F. (288° C.)).

In another embodiment, not shown, stream 420 is not combined with methanol diluted stream 418 prior to conversion thereof to light olefins. Instead, as discussed above with reference to FIG. 2, stream 420 is directed to an MTO reactor wherein the methanol contained in stream 420 contacts one or more molecular sieve catalyst compositions under conditions effective to convert the methanol contained therein to light olefins. Similarly, the ethanol contained in methanol diluted stream 418 can be directed to an ETO reactor wherein the ethanol contained therein contacts one or more molecular sieve catalyst compositions under conditions effective to convert the ethanol contained in the methanol diluted stream 418 to ethylene. In this manner, the reactor type and reaction conditions of the MTO reactor and the ETO reactor may differ in order to provide optimized reaction conditions for converting the methanol in stream 420 to light olefins and the ethanol in methanol diluted stream 418 to ethylene.

F. Controlling the Ratio of Ethylene to Propylene Formed in an OTO Reaction System It has been discovered that ethanol has a selectivity for ethylene under OTO and ETO reaction conditions, which approaches 100 weight percent. Methanol, in contrast, produces ethylene and propylene in generally equal amounts under OTO and ETO reaction conditions. By increasing the amount of ethanol contained in an OTO feedstock, the amount of ethylene produced in the OTO reaction system relative to propylene can be advantageously increased.

In one aspect of the invention, the ratio of ethylene to propylene formed in an OTO reaction system can be controlled by varying the ratio of the methanol to ethanol that is sent to the OTO reaction system. As indicated above, methanol converts to ethylene and propylene in relatively equal amounts in an OTO reaction system, while ethanol converts almost entirely to ethylene. As a result, as the amount of ethanol contained in an OTO feedstock is increased relative to methanol, the amount of ethylene produced in the OTO reaction system will increase. Thus, the amount of ethylene relative to propylene formed in an OTO reaction system advantageously can be controlled by controlling the ratio of methanol to ethanol contained in the OTO feedstock.

The weight ratio of methanol to ethanol contained in an OTO feedstock can be controlled by a variety of ways. For example, if the integrated system comprises a methanol synthesis unit that is separate from the ethanol synthesis unit, then one or more flow control devices may be used to control the flow of methanol from the methanol synthesis unit and the amount of ethanol from the ethanol synthesis unit that is directed to the OTO reaction system. Additionally or alternatively, the amount and/or type of catalyst in the ethanol synthesis unit and/or the methanol synthesis unit can be varied to control ratio of the alcohols formed therein. If the integrated system includes a single combined synthesis unit, which forms both the methanol and methanol, then the weight ratio of the methanol synthesis catalyst to the ethanol synthesis catalyst (e.g., homologation catalyst) contained in the combined synthesis unit can be controlled to provide a desired methanol to ethanol weight ratio.

Additionally or alternatively, the reaction conditions in the ethanol synthesis unit, e.g., temperature, can be varied to control ratio of the ethanol formed therein. Generally, an increase in reaction temperature in an ethanol synthesis unit, within reason, increases the amount of ethanol formed in the ethanol synthesis unit.

Thus, in one aspect of the invention, the ratio of ethylene to propylene formed in an OTO reaction system can be controlled by varying the reaction temperature in an ethanol synthesis unit, which, in cooperation with a methanol synthesis unit, produces the feedstock for the OTO reaction system. That is, an increase in the reaction temperature of an ethanol synthesis unit will increase the amount of ethanol formed, which, ultimately, will increase the amount of ethylene that is formed in the OTO reaction system. In this manner, the amount of ethylene relative to propylene formed in an OTO reaction system advantageously can be controlled by controlling the reaction temperature of the ethanol synthesis unit.

Table I, below, illustrates the relationship of temperature and ethanol production in one prophetic ethanol synthesis system. In the homologation zone of the ethanol synthesis system, the pressure was held at approximately 1400 psig (9653 kPag) and the gas hourly space velocity was held constant at approximately 2500 hr$^{-1}$. The catalyst implemented in the ethanol synthesis system was comprised of $K_2CO_3$/sulfided CoMo homologation catalyst. The feed to the homologation zone was comprised of methanol, CO, and $H_2$ in molar fractions of 0.128, 0.436, and 0.436, respectively. The ethanol synthesis system operated in parallel to a methanol synthesis unit, as described above with reference to FIG. 2.

TABLE I

Ethanol Production as a Function of Temperature

| Reaction Temperature ° F. (° C.) | Weight Percent Ethanol in OTO Feedstock |
|---|---|
| 450 (232) | 5.7 |
| 500 (260) | 7.7 |
| 550 (288) | 9.8 |

The data in Table I clearly confirms that as temperature is increased in a homologation zone, the amount of ethanol formed therein increases.

G. EXAMPLES

The present invention will be better understood in view of the following non-limiting examples.

Example I (Control)

Methanol as OTO Feedstock

In Example I, which is a control example, a feedstock comprising 99.5 weight percent methanol (~0.5 weight percent water) was directed to an OTO microflow reactor for conversion thereof to light olefins. The resulting effluent stream was then analyzed to determine the amount of ethylene relative to propylene formed in the microflow reactor. The amounts of other products formed in the microflow reactor were also determined.

A SAPO-34 molecular sieve catalyst composition, designated catalyst composition "A", was formulated following U.S. Pat. No. 6,440,894, the entirety of which is incorporated herein by reference. The silicon to aluminum atomic ratio of the as-synthesized SAPO-34 molecular sieve used to form the catalyst composition was determined to be 0.068 based on Inductively Coupled Plasma (ICP) spectroscopy analysis. The formulated catalyst composition had the following overall composition: 40 weight percent molecular sieve, 12 weight percent ACH (aluminum chlorhydrol) binder and with the rest (48 weight percent) being kaolin clay matrix material, based on the total weight of the formulated catalyst composition. For each run, 95 mg of the molecular sieve catalyst composition was mixed with 1 g of 100-μm silicon-carbide. The resulting mixture was loaded into the microflow reactor, which was made of 0.25 inch silicon-steel tubing. The reactor temperature was increased to the desired reaction temperature (475° C. for control Example I) while the catalyst was under He flow (46 ml/min), and was held at that temperature for about 30 to 40 minutes for temperature stabilization.

The oxygenate-containing feed was introduced into the reactor at 80 μl/min, 100 WHSV and 25 psig (175 kPag) while the effluent was sampled by a 16-loop Valco valve. The reactor effluent formed was sampled in a multi-loop sampling valve to obtain the gas phase selectivity data. From about 9 to 15 samples were analyzed for each set of conditions to obtain the weighed average selectivity. After each test run, oxygen/He was passed through the catalyst to measure the coke deposit.

A mixture of 10 ml/min of $O_2$ and 10 ml/min of helium was flowed through the reactor for catalyst regeneration while the reactor temperature was increased from 475° C. to 550° C. A portion of the regeneration gas stream was sent into a nickel-containing methanator, which converted CO and $CO_2$ in the effluent stream into methane in the presence of an excess amount of $H_2$. The concentration of methane was then quantified by a FID detector. The amount of coke on the removed sieve was then measured by comparing the integrated peak area from the FID detector with that of a calibration standard.

The collected effluent samples were analyzed by on-line gas chromatography (Hewlett Packard 6890) equipped with a flame ionization detector. The chromatographic column used was a Plot Q column.

The weighed averages (selectivities) of the effluent samples were calculated based on the following formula, $(x_1)(y_1)+(x_2-x_1)(y_2)+(x_3-x_2)(y_2+y_3)/2+(x_4-x_3)(y_3+y_4)/2+\ldots$, where $x_i$ and $y_i$ are yield and g methanol fed/g sieve, respectively. Catalyst Lifetime (g/g catalyst) reported is methanol that was cumulatively converted. Note that both the lifetime and WHSV were reported based on the weight of the sieve. Methanol converted at less than about 10 weight percent conversion was not included in the calculations.

Coke selectivities were calculated based on the FID measurement of the end-of-run coke (EOR) and the catalyst lifetime, i.e., Coke selectivity, weight percent=EOR coke (g coke/g sieve)/{lifetime (g methanol/g sieve)*14/32 (g $CH_2$/g methanol)}*100.

The selectivity of methanol conversion to the various products were determined through gas chromatography. The results are provided in Table II, below. The data provided in each of the columns of Table II (except Reaction Temperature and Catalyst Lifetime, which is recorded in g/g catalyst) are weight percentages, based on the total weight of the effluent produced. $C_1$, $C_2^=$, $C_2^0$, $C_3^=$, $C_3^0$, ACAD, $C_4+$, $C_2^=+C_3^=$ in the following Tables refer to methane, ethylene, ethane, propylene, propane, acetaldehyde, hydrocarbons containing four or more carbon atoms, and ethylene and propylene combined, respectively.

As indicated above, the prime olefin selectivity (POS) for the conversion of a feedstock comprising pure 90 weight percent methanol and 10 weight percent ethanol ranged from 68.47 to 78.79 depending on reaction temperature. The ratio of ethylene to propylene formed ranged from 1.09 to 1.54 also depending on reaction temperature.

The data from this example illustrates a surprising and unexpected flexibility in the ability to tune the ratio of ethylene to propylene formed in an OTO reaction system by modifying the reaction temperature when the feedstock comprises a mixture of methanol and ethanol. For example, the ethylene to propylene ratio increased from 0.92 to 1.25 with the 10 weight percent ethanol/90 weight percent methanol feedstock, which is an increase of 36 percent. Further-

TABLE II

Selectivity and Conversion of Feedstock Comprising 100 Wt. Percent Methanol to Light Olefins

| Reaction Temp. | $C_1$ | $C_2^=$ | $C_2^0$ | $C_3^=$ | $C_3^0$ | ACAD | $C_4+$ | Coke | $C_2^=+C_3^=$ | $C_2^=/C_3^=$ | Catalyst Lifetime |
|---|---|---|---|---|---|---|---|---|---|---|---|
| 475° C. | 1.61 | 35.94 | 0.28 | 39.20 | 0.61 | — | 22.34 | 2.28 | 75.13 | 0.92 | 20.50 |

As indicated in Table II, above, the prime olefin selectivity (POS) for the conversion of a pure methanol feedstock at 475° C., 25 psig and 100 WHSV was 75.13 weight percent. The ratio of ethylene to propylene formed was 0.92.

Example II

9:1 Methanol to Ethanol Wt. Ratio in OTO Feedstock

In Example II, a feedstock comprising 90 weight percent methanol and 10 weight percent ethanol was directed to an OTO microflow reactor for conversion thereof to light olefins. The oxygenate-containing feed was introduced into the reactor containing Catalyst Composition A under the same conditions as indicated above for Example I (100 WHSV and 25 psig (175 kPag)). Unlike Example I, however, 9 to 15 runs were performed for each of the following reaction temperatures: 425° C., 450° C., 475° C. and 500° C. to determine what effect, if any, temperature had on conversion and selectivity of a mixed alcohol-containing feedstock to light olefins.

The resulting effluent stream was then analyzed in the manner described above in Example I to determine the amount of ethylene relative to propylene that was formed in the OTO reactor. The amounts of other products formed in the microflow reactor were also determined. The results of the analysis are indicated below in Table III.

more, the data from this example at 475° C. illustrates that the overall POS also improved with the 10 weight percent ethanol/90 weight percent methanol feedstock when compared with the pure methanol feed that was conducted under the same experimental conditions in Example I. For example, the POS for the mixed feed was 78.92 weight percent, an increase of 5 percent. More importantly, the ethylene selectivity increased by 22 percent (or 7.92 weight percent) with the 10 weight percent ethanol/90 weight percent methanol feedstock.

Example III

8:2 Methanol to Ethanol Ratio in OTO Feedstock

In Example III, a feedstock comprising 80 weight percent methanol and 20 weight percent ethanol was directed to an OTO microflow reactor for conversion thereof to light olefins. The oxygenate-containing feed was introduced into the reactor containing Catalyst Composition A under the same conditions as indicated above for Example I (100 WHSV and 25 psig (175 kPag)). Unlike Example I, however, runs were performed for each of the following reaction temperatures: 450° C., 475° C. and 500° C. to determine what effect, if any, temperature had on conversion and selectivity of a mixed alcohol-containing feedstock to light olefins.

TABLE III

Selectivity and Conversion of Feedstock Comprising 90 Wt. Percent Methanol and 10 Wt. Percent Ethanol to Light Olefins

| Reaction Temp. | $C_1$ | $C_2^=$ | $C_2^0$ | $C_3^=$ | $C_3^0$ | ACAD | $C_4+$ | Coke | $C_2^=+C_3^=$ | $C_2^=/C_3^=$ | Catalyst Lifetime |
|---|---|---|---|---|---|---|---|---|---|---|---|
| 425° C. | 1.00 | 35.66 | 0.21 | 32.81 | 0.39 | 3.24 | 25.26 | 1.44 | 68.47 | 1.09 | 33.28 |
| 450° C. | 1.12 | 39.99 | 0.22 | 35.83 | 0.37 | 1.39 | 20.06 | 1.00 | 75.83 | 1.12 | 46.73 |
| 475° C. | 1.23 | 43.86 | 0.30 | 35.07 | 0.44 | 0.97 | 16.78 | 1.35 | 78.92 | 1.25 | 31.38 |
| 500° C. | 2.47 | 47.76 | 0.45 | 31.03 | 0.42 | 1.63 | 14.11 | 2.13 | 78.79 | 1.54 | 20.49 |

The resulting effluent stream was then analyzed in the manner described above in Example I to determine the amount of ethylene relative to propylene that was formed in the OTO reactor. The amounts of other products formed in the microflow reactor were also determined. The results of the analysis are indicated below in Table IV.

TABLE IV

Selectivity and Conversion of Feedstock Comprising
80 Wt. Percent Methanol and 20 Wt. Percent Ethanol to Light Olefins

| Reaction Temp. | $C_1$ | $C_2^=$ | $C_2^0$ | $C_3^=$ | $C_3^0$ | ACAD | $C_4+$ | Coke | $C_2^= + C_3^=$ | $C_2^=/C_3^=$ | Catalyst Lifetime |
|---|---|---|---|---|---|---|---|---|---|---|---|
| 450° C. | 0.79 | 46.01 | 0.27 | 30.65 | 0.38 | 2.42 | 18.18 | 1.29 | 76.67 | 1.51 | 37.59 |
| 475° C. | 0.99 | 47.98 | 0.35 | 30.17 | 0.43 | 2.21 | 15.92 | 1.95 | 78.15 | 1.59 | 22.63 |
| 500° C. | 2.30 | 52.57 | 0.50 | 24.30 | 0.30 | 4.80 | 12.79 | 2.45 | 76.87 | 2.16 | 26.61 |

The data from this example also illustrates a surprising and unexpected flexibility in the ability to tune the ratio of ethylene to propylene formed in an OTO reaction system by modifying the reaction temperature when the feedstock comprises a mixture of methanol and ethanol. For example, the ethylene to propylene ratio increased from 0.92 to 1.59 with the 20 weight percent ethanol/80 weight percent methanol feedstock, which is an increase of 73 percent. When the reaction temperature was raised to 500° C., the ethylene/propylene ratio reached 2.16, a surprising and unexpected breakthrough as far as the economics of the process are concerned. The ethylene selectivity at 475° C. increased by about 34 percent (or 12 weight percent) over control when the feedstock contained 20 weight percent ethanol and 80 weight percent methanol.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for producing light olefins, the process comprising the steps of:
   (a) contacting syngas in the presence of one or more metal-containing catalysts to produce a first feedstock comprising methanol;
   (b) converting a portion of the methanol in a homologation zone to a second feedstock comprising ethanol by contacting the portion of the methanol with a homologation catalyst selected from the group consisting of potassium oxides, cobalt-molybdenum sulfides, nickel-molybdenum sulfides and potassium carbonates; and
   (c) introducing the first feedstock and the second feedstock to a process for converting the methanol and the ethanol in the presence of a silicoaluminophosphate molecular sieve catalyst composition to the light olefins, wherein the combined feedstock has a methanol to ethanol weight ratio of from 4.0:1.0 to 19.0:1.0 and the process for converting the methanol and the ethanol to light olefins is carried out at a temperature of from 475° C. to 500° C.

2. The process of claim 1, wherein the second feedstock further comprises methanol.

3. The process of claim 1, wherein the process further comprises the step of:
   (d) combining the first feedstock and the second feedstock to form a combined feedstock prior to converting in the presence of the catalyst.

4. The process of claim 3, wherein the combined feedstock comprises methanol, ethanol and water.

5. The process of claim 4, wherein the process further comprises the step of:
   (e) removing a weight majority of the water from the combined feedstock prior to converting in the presence of the catalyst.

6. The process of claim 4, wherein the combined feedstock further comprises light ends, the process further comprising the step of:
   (e) removing the light ends from at least a portion of the combined feedstock, wherein the light ends comprise carbon monoxide, methane and hydrogen.

7. The process of claim 1, wherein the molecular sieve catalyst composition comprises a molecular sieve selected from the group consisting of: SAPO-5, SAPO-8, SALPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

8. The process of claim 1, wherein step (b) further comprises contacting the portion of the methanol with the homologation catalyst in the presence of carbon monoxide, optionally hydrogen and optionally carbon dioxide.

9. The process of claim 8, wherein the process for converting the methanol and the ethanol in the presence of a molecular sieve catalyst composition to the light olefins also produces carbon monoxide, wherein the carbon monoxide is separated from the light olefins and is directed to the homologation zone to provide a carbon monoxide source for step (b).

10. The process of claim 1, wherein the one or more metal-containing catalysts comprises one or more of copper oxides, zinc oxides and aluminum oxides.

11. The process of claim 1, wherein the process further comprises the step of:
   (d) contacting a natural gas stream with oxygen under conditions effective to convert the natural gas stream into the syngas.

12. An integrated process for producing light olefins, the process comprising the steps of:
   (a) contacting syngas with one or more metal-containing catalysts to produce a first feedstock comprising methanol;
   (b) contacting a portion of the methanol with carbon monoxide in the presence of a catalyst system containing a catalyst selected from the group consisting of potassium oxides, cobalt-molybdenum sulfides, nickel-molybdenum sulfides and potassium carbonates to produce a second feedstock comprising ethanol; and (c) introducing the first feedstock and the second feedstock to a process for converting the methanol and the ethanol in the presence of a silicoaluminophosphate molecular sieve catalyst composition to the light olefins, wherein the combined feedstock has a methanol to ethanol weight ratio of from 4.0:1.0 to 19.0:1.0 and the process for convening the methanol and the ethanol to light olefins is carried our at a temperature of from 475°C. to 500° C.

13. The integrated process of claim 12, wherein the second feedstock further comprises methanol.

14. The integrated process of claim 12, wherein the process further comprises the step of:
(d) combining the first feedstock and the second feedstock to form a combined feedstock prior to converting in the presence of the catalyst.

15. The integrated process of claim 14, wherein the combined feedstock comprises methanol, ethanol and water.

16. The integrated process of claim 15, wherein the process further comprises the step of:
(e) removing a weight majority of the water from the combined feedstock prior to converting in the presence of the catalyst.

17. The integrated process of claim 15, wherein the combined feedstock further comprises light ends, the process further comprising the step of:
(e) removing the light ends from at least a portion of the combined feedstock, wherein the light ends comprise carbon monoxide, methane and hydrogen.

18. The integrated process of claim 12, wherein the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

19. The integrated process of claim 12, wherein the one or more metal-containing catalysts comprises one or more of copper oxides, zinc oxides and aluminum oxides.

20. The integrated process of claim 12, wherein the process further comprises the step of:
(d) contacting a natural gas stream with oxygen under conditions effective to convert the natural gas stream into the syngas.

21. A process for producing light olefins, the process comprising the steps of:
(a) contacting a syngas stream with a methanol synthesis catalyst under first conditions effective to form a methanol-containing stream comprising methanol;
(b) contacting at least a portion of the methanol-containing stream with carbon monoxide and a homologation catalyst selected from the group consisting of potassium oxides, cobalt-molybdenum sulfides, nickel-molybdenum sulfides and potassium carbonates and forming a mixed alcohol stream comprising methanol and ethanol at a methanol to ethanol weight ratio of from 4.0:1.0 to 19.0:1.0; and
(c) contacting at least a portion of the mixed alcohol stream with a silicoaluminophosphate molecular sieve catalyst composition at a temperature of from 475° C. to 500° C. to convert the methanol and the ethanol to the light olefins.

22. The process of claim 21, wherein the mixed alcohol stream further comprises water, the process further comprising the step of:
(d) separating a weight majority of the water from the mixed alcohol stream.

23. The process of claim 21, wherein the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

24. The process of claim 21, wherein the methanol synthesis catalyst is selected from the group consisting of: copper oxides, zinc oxides and aluminum oxides.

25. The process of claim 21, wherein the mixed alcohol stream further comprises light ends, the process further comprising the step of:
d) removing the light ends from at least a portion of the mixed alcohol stream, wherein the light ends comprise carbon monoxide, methane and hydrogen.

26. The process of claim 21, wherein the process further comprises the step of:
d) separating the mixed alcohol stream into a first fraction and a second fraction, wherein the first fraction comprises a weight majority of the methanol present in the mixed alcohol stream, and wherein the second fraction comprises a weight majority of the ethanol present in the mixed alcohol stream.

27. The process of claim 21, wherein the process further comprises the step of:
(d) contacting a natural gas stream with oxygen under conditions effective to convert the natural gas stream into the syngas stream.

28. A process for producing light olefins, wherein the process comprises the steps of:
(a) contacting a syngas stream comprising carbon monoxide, hydrogen and optionally carbon dioxide with a methanol synthesis catalyst under first conditions effective to form a methanol-containing steam comprising methanol and water;
(b) contacting at least a portion of the methanol-containing stream with carbon monoxide and a homologation catalyst selected from the group consisting of potassium oxides, cobalt-molybdenum sulfides, nickel-molybdenum sulfides and potassium carbonates and forming a mixed alcohol stream comprising methanol and ethanol at a methanol to ethanol weight ratio of from 4.0:1.0 to 19.0:1.0;
(c) contacting at least a portion of the mixed alcohol stream with a silicoaluminophosphate molecular sieve catalyst composition in a reaction system at a temperature of from 475° C. to 500° C. to convert the methanol and ethanol to light olefins;
(d) yielding an effluent stream from the reaction system, wherein the effluent stream has an ethylene to propylene weight ratio of about from about 0.9:1.0 to about 2.2:1.0.

29. The process of claim 28, wherein the ethylene to propylene weight ratio is from about 1.1:1.0 to about 1.4:1.0.

30. The process of claim 28, wherein the process further comprises the step of:
(e) removing a weight majority of the water from the mixed alcohol stream.

31. The process of claim 28, wherein the molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

32. The process of claim 28, wherein the methanol synthesis catalyst is selected from the group consisting of: copper oxides, zinc oxides and aluminum oxides.

33. The process of claim 28, wherein the process further comprises the step of:

(e) removing light ends from at least a portion of the mixed alcohol stream, wherein the light ends comprise carbon monoxide and hydrogen.

34. The process of claim 28, wherein the process further comprises the step of:

(e) contacting a natural gas stream with oxygen under conditions effective to convert the natural gas stream into the syngas stream.

* * * * *